(12) United States Patent
Ren et al.

(10) Patent No.: US 10,508,303 B2
(45) Date of Patent: Dec. 17, 2019

(54) WHOLE-GENOME AND TARGETED HAPLOTYPE RECONSTRUCTION

(71) Applicant: Ludwig Institute for Cancer Research, New York, NY (US)

(72) Inventors: Bing Ren, La Jolla, CA (US); Siddarth Selvaraj, La Jolla, CA (US); Jesse Dixon, La Jolla, CA (US); Anthony Schmitt, La Mesa, CA (US)

(73) Assignee: LUDWIG INSTITUTE FOR CANCER RESEARCH LTD, Zurich (CH)

( * ) Notice: Subject to any disclaimer, the term of this patent is extended or adjusted under 35 U.S.C. 154(b) by 329 days.

(21) Appl. No.: 14/906,153

(22) PCT Filed: Jul. 18, 2014

(86) PCT No.: PCT/US2014/047243
§ 371 (c)(1),
(2) Date: Jan. 19, 2016

(87) PCT Pub. No.: WO2015/010051
PCT Pub. Date: Jan. 22, 2015

(65) Prior Publication Data
US 2016/0160275 A1 Jun. 9, 2016

Related U.S. Application Data

(60) Provisional application No. 61/873,671, filed on Sep. 4, 2013, provisional application No. 61/856,486, filed on Jul. 19, 2013.

(51) Int. Cl.
| | | |
|---|---|---|
| C12Q 1/68 | (2018.01) | |
| C12Q 1/6874 | (2018.01) | |
| C12Q 1/6869 | (2018.01) | |

(52) U.S. Cl.
CPC ......... *C12Q 1/6874* (2013.01); *C12Q 1/6869* (2013.01)

(58) Field of Classification Search
None
See application file for complete search history.

(56) References Cited

U.S. PATENT DOCUMENTS

| | | |
|---|---|---|
| 9,434,985 B2 | 9/2016 | Dekker et al. |
| 2007/0172853 A1 | 7/2007 | McCarroll et al. |
| 2012/0220494 A1 | 8/2012 | Samuels et al. |

FOREIGN PATENT DOCUMENTS

WO     2012106546 A2     8/2012

OTHER PUBLICATIONS

Shendure et al.: "The Expanding Scope of DNA Sequencing"; Nov. 8, 2012, Nat Biotechnol, vol. 30, No. 11, pp. 1084-1094.
Lieberman-Aiden et al.: "Comprehensive Mapping of Long Range Interactions Reveals Folding Principles of the Human Genome"; Oct. 9, 2009, Science, vol. 326, pp. 289-293.
Selvaraj, et al.: "Whole-Genome Haplotype Reconstruction Using Proximity-Ligation and Shotgun Sequencing", Nature Biotechnology, Nov. 3, 2013, vol. 31, pp. 1111-1118.
International Search Report and Written Opinion for PCT International Application No. PCT/US2014/047243 dated Nov. 24, 2014.

*Primary Examiner* — Katherine D Salmon
(74) *Attorney, Agent, or Firm* — Fox Rothschild LLP

(57) ABSTRACT

The present invention relates to methods for haplotype determination and, m particular, haplotype determination at the whole genome level as well as targeted haplotype determination.

18 Claims, 19 Drawing Sheets b)

| Chr | Phasable Span of Chr | Variants spanned in MVP block | %Chr Spanned in MVP block | %Variants Phased in MVP block | % Accuracy of variants phased in MVP block |
|---|---|---|---|---|---|
| chr1 | 104,188,030 | 1,409,566 | 100.000 | 95.231 | 99.627 |
| chr2 | 178,746,638 | 1,109,866 | 99.997 | 93.703 | 99.569 |
| chr3 | 156,599,306 | 1,120,125 | 100.000 | 94.911 | 99.639 |
| chr4 | 152,628,848 | 1,030,740 | 99.997 | 94.366 | 99.546 |
| chr5 | 149,536,169 | 1,063,616 | 99.939 | 94.414 | 99.521 |
| chr6 | 146,516,752 | 1,074,301 | 100.000 | 96.086 | 99.674 |
| chr7 | 149,523,520 | 965,142 | 99.999 | 94.152 | 99.427 |
| chr8 | 128,735,517 | 939,132 | 99.948 | 95.060 | 99.558 |
| chr9 | 121,070,077 | 832,047 | 99.987 | 94.547 | 99.600 |
| chr10 | 126,991,341 | 980,549 | 99.996 | 95.624 | 99.735 |
| chr11 | 118,843,488 | 861,541 | 99.999 | 94.612 | 99.577 |
| chr12 | 118,256,511 | 794,128 | 100.000 | 94.588 | 99.515 |
| chr13 | 117,284,037 | 858,859 | 100.000 | 95.494 | 99.679 |
| chr14 | 122,159,750 | 823,216 | 99.998 | 94.707 | 99.541 |
| chr15 | 100,494,041 | 719,897 | 100.000 | 94.811 | 99.618 |
| chr16 | 95,301,285 | 711,670 | 99.898 | 95.471 | 99.658 |
| chr17 | 92,272,062 | 616,348 | 99.999 | 93.669 | 99.443 |
| chr18 | 87,771,251 | 674,750 | 99.989 | 95.631 | 99.599 |
| chr19 | 58,256,454 | 411,457 | 99.869 | 95.243 | 99.662 |

FIG. 3B b)

| Chr | % Chr Spanned in MVP block | % Variants Phased in MVP block | % Accuracy of variants phased in MVP block |
|---|---|---|---|
| chr1 | 99.932 | 33.428 | 99.223 |
| chr2 | 99.975 | 30.650 | 99.298 |
| chr3 | 99.975 | 32.522 | 99.079 |
| chr4 | 99.913 | 30.948 | 98.994 |
| chr5 | 99.947 | 30.259 | 99.310 |
| chr6 | 99.982 | 35.529 | 99.223 |
| chr7 | 99.909 | 30.841 | 99.227 |
| chr8 | 99.879 | 32.273 | 99.234 |
| chr9 | 99.932 | 31.676 | 99.338 |
| chr10 | 99.997 | 34.246 | 99.318 |
| chr11 | 99.997 | 30.736 | 99.334 |
| chr12 | 99.931 | 31.056 | 99.061 |
| chr13 | 99.988 | 33.793 | 99.256 |
| chr14 | 99.627 | 31.723 | 99.106 |
| chr15 | 99.847 | 33.108 | 99.168 |
| chr16 | 99.483 | 33.586 | 99.255 |
| chr17 | 99.920 | 31.240 | 99.213 |
| chr18 | 99.775 | 33.775 | 99.174 |
| chr19 | 99.285 | 32.464 | 99.086 |

FIG. 4B c)

| Chr | % Phasable Span of Chr. | Variants spanned in MVP block | % Chr spanned in MVP block | % Variants phased in MVP block |
|---|---|---|---|---|
| chr1 | 247,195,920 | 161,669 | 99.911 | 21.596 |
| chr2 | 242,747,622 | 174,845 | 99.984 | 22.766 |
| chr3 | 199,384,702 | 144,914 | 99.986 | 23.915 |
| chr4 | 191,260,971 | 151,304 | 99.974 | 24.687 |
| chr5 | 180,770,319 | 139,987 | 99.890 | 24.037 |
| chr6 | 170,883,965 | 146,307 | 99.924 | 28.113 |
| chr7 | 158,765,244 | 123,880 | 99.992 | 22.819 |
| chr8 | 146,268,969 | 115,878 | 99.912 | 24.457 |
| chr9 | 140,252,520 | 95,981 | 99.936 | 22.347 |
| chr10 | 135,321,315 | 108,910 | 99.976 | 22.544 |
| chr11 | 134,358,758 | 104,211 | 99.984 | 24.144 |
| chr12 | 132,273,383 | 99,405 | 99.997 | 21.511 |
| chr13 | 96,209,726 | 76,991 | 99.495 | 24.260 |
| chr14 | 88,283,606 | 68,949 | 99.973 | 21.751 |
| chr15 | 82,077,797 | 61,540 | 99.979 | 22.164 |
| chr16 | 88,818,477 | 71,478 | 99.847 | 21.507 |
| chr17 | 78,612,598 | 54,660 | 99.745 | 18.862 |
| chr18 | 76,114,907 | 61,146 | 99.956 | 22.791 |
| chr19 | 63,773,223 | 50,151 | 99.726 | 16.706 |
| chr20 | 62,424,237 | 49,535 | 99.745 | 22.572 |
| chr21 | 37,193,100 | 31,891 | 99.822 | 22.223 |
| chr22 | 35,158,263 | 32,300 | 99.929 | 16.464 |
| chrX | 151,825,709 | 64,769 | 99.982 | 15.765 |

FIG. 4C

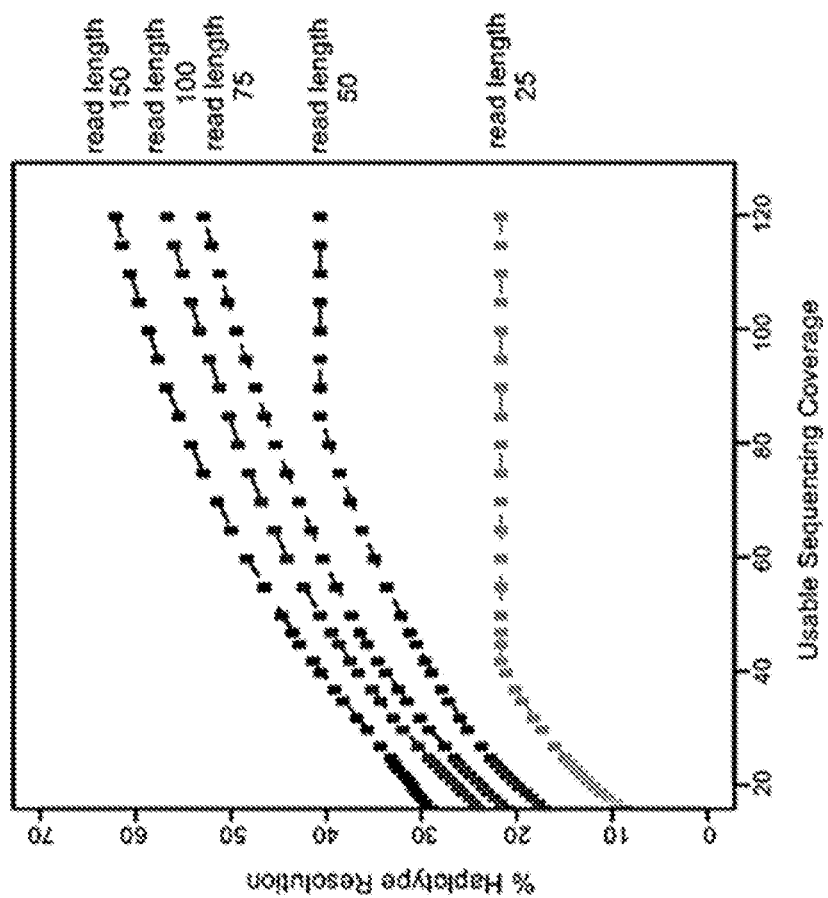
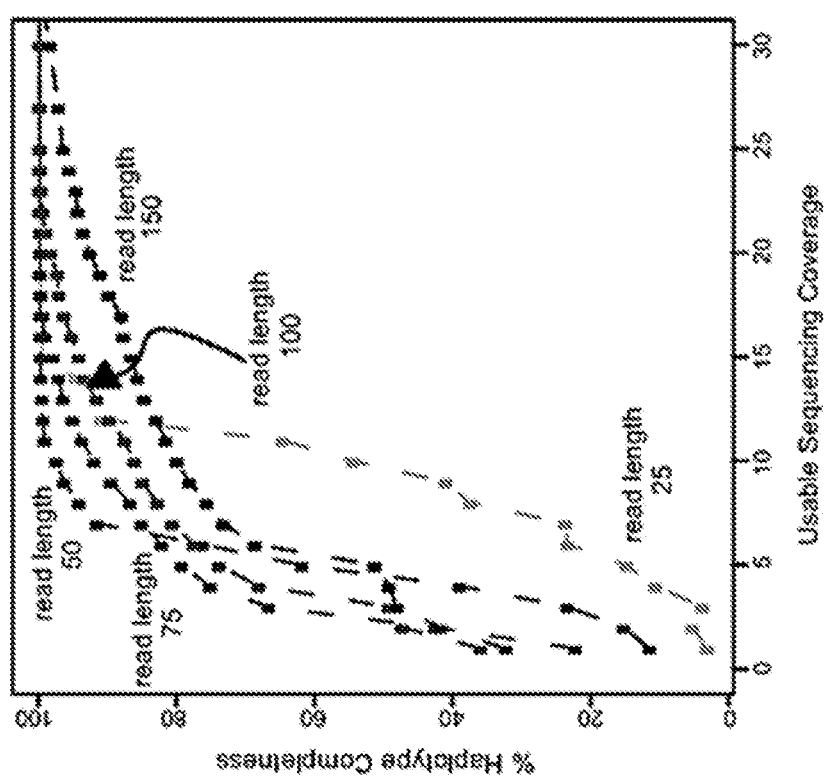
FIG. 5D
FIG. 5C

Completeness = Span of the MVP block
= 75/78 = 96.15%

Resolution = #Het. Variants phased in MVP block / #Het. Variants spanned in MVP block
= 11/13 = 84.6%

Accuracy = Correctly Phased het. variants in the MVP block
= 10/11 = 90.9%

WHOLE-GENOME AND TARGETED HAPLOTYPE RECONSTRUCTION

CROSS REFERENCE TO RELATED APPLICATIONS

This application is the U.S. National Phase of International Patent Application Serial No. PCT/US14/47243 filed Jul. 18, 2014 which claims the benefit of priority under 35 U.S.C. § 119(e) of U.S. provisional No. 61/856,486 filed on Jul. 19, 2013, and U.S. Provisional Application No. 61/873,671 filed on Sep. 4, 2013, the disclosures of which are incorporated herein by reference in their entireties.

FIELD OF THE INVENTION

This invention relates to methods for haplotype determination and, in particular, haplotype determination at the whole genome level as well as targeted haplotype determination.

BACKGROUND OF THE INVENTION

Rapid progress in DNA shotgun sequencing technologies has enabled systematic identification of the genetic variants of an individual (Wheeler et al., Nature 452, 872-876 (2008); Pushkarev et al., Nature Biotechnology 27, 847-850 (2009); Kitzman et al., Science Translational Medicine 4, 137ra176 (2012); and Levy et al., Plos Biology 5, e254 (2007)). However, as the human genome consists of two homologous sets of chromosomes, understanding the true genetic makeup of an individual requires delineation of the maternal and paternal copies, or haplotypes, of the genetic material. The utility of obtaining a haplotype in an individual can be several fold: first, haplotypes are useful clinically in predicting outcomes for donor-host matching in organ transplantation (Crawford et al., Annual Review Of Medicine 56, 303-320 (2005) and Petersdorf et al., PLoS Medicine 4, e8 (2007)) and are increasingly used as a means to detect disease associations (Studies et al., Nature 447, 655-660 (2007); Cirulli, et al., Nature Reviews. Genetics 11, 415-425 (2010); and Ng et al., Nature Genetics 42, 30-35 (2010)). Second, in genes that show compound heterozygosity, haplotypes provide information as to whether two deleterious variants are located on the same or different alleles, greatly impacting the prediction of whether inheritance of these variants are deleterious (Musone et al., Nature Genetics 40, 1062-1064 (2008); and Erythematosus, et al., Nature Genetics 40, 204-210 (2008); and Zschocke, Journal of Inherited Metabolic Disease 31, 599-618 (2008)). In complex genomes such as humans, compound heterozygosity may involve genetic or epigenetic variations at noncoding cis-regulatory sites located far from the genes they regulate (Sanyal et al., Nature 489, 109-113 (2012)), underscoring the importance of obtaining chromosome-span haplotypes. Third, haplotypes from groups of individuals have provided information on population structure (International HapMap, C. et al., Nature 449, 851-861 (2007); Genomes Project, C. et al., Nature 467, 1061-1073 (2010); and Genomes Project, C. et al., Nature 491, 56-65 (2012)), and the evolutionary history of the human race (Meyer et al., Science 338, 222-226 (2012)). Lastly, recently described widespread allelic imbalances in gene expression suggest that genetic or epigenetic differences between alleles may contribute to quantitative differences in expression (Gimelbrant et al., Science 318, 1136-1140 (2007); Kong et al., Nature 462, 868-874 (2009); Xie et al., Cell 148, 816-831 (2012); and McDaniell et al., Science 328, 235-239 (2010)). An understanding of haplotype structure will therefore be critical for delineating the mechanisms of variants that contribute to these allelic imbalances. Taken together, knowledge of complete haplotype structure in individuals is essential for advancing personalized medicine.

Recognizing the importance of haplotypes, several groups have sought to expand the understanding of haplotype structures both at the level of populations and individuals. Initiatives such as International Hapmap project and 1000 genomes project have attempted to systematically reconstruct haplotypes through linkage disequilibrium measures based on populations of unrelated individuals sequencing data or by genotyping family trios. However, the average length of accurately phased haplotypes generated using this approach is limited to ~300 kb (Fan et al., Nature Biotechnology 29, 51-57 (2011) and Browning et al., American Journal of Human Genetics 81, 1084-1097 (2007)). Numerous experimental methods have also been developed to facilitate haplotype phasing of an individual, including LFR sequencing, mate-pair sequencing, fosmid sequencing, and dilution-based sequencing (Levy et al., PLoS Biology 5, e254 (2007); Bansal et al., Bioinformatics 24, i153-159 (2008); Kitzman et al., Nature Biotechnology 29, 59-63 (2011); Suk et al., Genome Research 21, 1672-1685 (2011); Duitama et al., Nucleic Acids Research 40, 2041-2053 (2012); and Kaper et al., Proc Natl Acad Sci USA 110, 5552-5557 (2013)). At best, these methods can reconstruct haplotypes ranging from several kilobases to about a megabase, but none can achieve chromosome-span haplotypes. Whole chromosome haplotype phasing has been achieved using Fluorescence Assisted Cell Sorting (FACS) based sequencing, chromosome-segregation followed by sequencing and chromosome micro-dissection based sequencing (Fan et al., Nature Biotechnology 29, 51-57 (2011); Yang et al., Proceedings of the National Academy of Sciences of the United States of America 108, 12-17 (2011); and Ma et al., Nature Methods 7, 299-301 (2010)). However, these methods are low resolution as they could phase only a fraction of the heterozygous variants in an individual, and more importantly, they are technically challenging to perform or require specialized instruments. Recently, whole genome haplotyping has been performed using genotyping from sperm cells (Kirkness et al., Genome Research 23, 826-832 (2013)). Although this approach can generate chromosome-span haplotypes at high resolution, it is not applicable to the general population and needs deconvolution of complex meiotic recombination patterns.

Along with whole-genome haplotyping, targeted haplotyping are also of importance. In particular, targeted haplotyping of HLA (Humnan leukocyte antigen) locus can aid in host-donor matching for organ transplantation and elucidating roles of cis-regulatory elements in gene activity.

Computational analysis has shown that an important factor in haplotype reconstruction from previously established DNA shotgun sequencing methods is the length of the sequenced genomic fragment (Tewhey et al., Nature Reviews. Genetics 12, 215-223 (2011)). For example, longer haplotypes can be obtained by mate pair sequencing (fragment or insert size~5 kb) compared with conventional genome sequencing (fragment or insert size~500 bp). However, there are technical limitations on how long these fragments can be. For instance, it is difficult to clone DNA fragments that are longer than what is obtained using fosmid clones. Hence, using existing shotgun sequencing approaches, it is difficult to generate haplotype blocks beyond 1 million bases, even at ultra-deep sequencing coverage.

Thus, there is a need for a method for reconstructing haplotypes at the whole genome level, as well as a method for targeted haplotyping.

SUMMARY OF INVENTION

This invention addresses the aforementioned unmet need by providing a method of reconstructing haplotype at the whole genome level, as well as a method of reconstructing haplotype at a targeted region of a genome.

Accordingly, the invention features a method for whole-chromosome haplotyping of an organism. The method includes providing a cell of the organism that contains a set of chromosomes having genomic DNA; incubating the cell or the nuclei thereof with a fixation agent for a period of time and restricting the fixated DNA with a restriction enzyme in order to allow proximity-ligation of the genomic DNA in situ and thereby to form ligated genomic DNA; fragmenting the ligated genomic DNA to form a proximally ligated complex having a first genomic DNA fragment and a second genomic DNA fragment; obtaining a plurality of the proximally-ligated DNA fragments to form a library; sequencing the plurality of the proximally-ligated DNA fragments to obtain a plurality of sequence reads and assembling the plurality of sequence reads to construct a chromosome-span haplotype for one or more of the chromosomes.

The invention further provides a method for targeted haplotyping of an organism. The method includes providing a cell of the organism that contains a set of chromosomes having genomic DNA; incubating the cell or the nuclei thereof with a fixation agent for a period of time and restricting the fixated DNA with a restriction enzyme in order to allow proximity-ligation of the genomic DNA in situ and thereby to form ligated genomic DNA; fragmenting the ligated genomic DNA to form a proximally-ligated complex having a first genomic DNA fragment and a second genomic DNA fragment; contacting the proximally-ligated DNA fragments with one or more oligonucleotides that hybridize to pre-selected regions of a subset of the proximally-ligated fragments to provide a subset of proximally-ligated fragments hybridized to the oligonucleotides, separating the subset of proximally-ligated fragments from the oligonucleotides; sequencing the subset of proximally-ligated DNA fragments to obtain a plurality of sequence reads and assembling the plurality of sequence reads to construct a targeted haplotype. In one embodiment, the oligonucleotides are immobilized.

In certain embodiments, the methods further include isolating the cell nuclei from the cell before the incubating step. Methods for isolating cell nuclei are known in the art. For example, methods for isolating nuclei from plant cells are disclosed by Lee et al. (2007) *The Plant Cell* 19:731-749.

In some embodiments, the methods further include purifying ligated genomic DNA before the fragmenting step. In other embodiments, the methods further include, after the fragmenting step, labeling the first genomic DNA fragment or the second genomic DNA fragment with a marker; joining the first genomic DNA fragment and the second genomic DNA fragment so that the marker is therebetween to form a labeled chimeric DNA molecule; and shearing the labeled chimeric DNA molecule to form labeled, proximally-ligated DNA fragments.

In the above methods, the fragmenting step can be carried out by various ways known in the art. For example, it can be carried out via enzymatic cleavage, including those mediated by, restriction enzymes, DNAse, or transposase. In one embodiment, this step is performed by digesting the ligated genomic DNA with a restriction enzyme to form digested genomic DNA fragments. Any suitable restriction enzymes (e.g., BamHI, EcoRI, HindIII, NcoI, or XhoI) or a combination of two or more such restriction enzymes can be used. The fixation agent can comprise formaldehyde, glutaraldehyde, or formalin. The labeling step can be carried out by filling the ends of said first or second genomic DNA fragment with a nucleotide that is labeled with the marker, e.g., biotin. In that case, the obtaining step can be carried out using streptavidin, which can be affixed to a bead. For the joining step, it can be carried out by ligating the first genomic DNA fragment and the second genomic DNA fragment using a ligase. The ligating step may be performed in solution or on a solid substrate. Ligation on a solid substrate is referred to herein as "tethered chromosomal capture." For the sequencing, it can be carried out using pair-end sequencing.

In one embodiment of the invention, each paired-end sequencing read fragment can be at least 20 bp in length, such as 20-1000 bp or preferably 20-150 bp in length (e.g., 20, 25, 30, 40, 50, 60, 60, 80, 90, 100, 110, 120, 130, 140, or 150 bp in length). For haplotyping each chromosome, the library contains at least 15× sequence coverage, e.g., 25-30× sequence coverage. Preferably, the first genomic DNA fragment and the second genomic DNA fragment are on the same chromosome or in cis. Preferably, the first genomic DNA fragment and the second genomic DNA fragment are apart in situ by at least 100 bp, such as 100-100 MB (e.g., 100 bp, 1 kb, 10 kb, 1 Mb, 10 Mb, 20 Mb, 30 Mb, 40 Mb, 50 Mb, 60 Mb, 70 Mb, 80 Mb, 90 Mb, or 100 Mb).

The method can be used on various organisms, including procaryotes and eucaryotes. The organisms include fungi, plants, and animals. In one preferred embodiment the organism is a plant. In another preferred embodiment, the organism is a mammal or a mammalian embryo, or a human or a human embryo. In one embodiment, the human is a donor or a recipient of an organ. In that case, the organ can be haplotyped using the method of this invention before being transplanted to a recipient with matching haplotype. The method of this invention can be used on a diploid cell, aneuploid cell, or a polyploid cell, e.g., certain cancerous cells.

The details of one or more embodiments of the invention are set forth in the description below. Other features, objects, and advantages of the invention will be apparent from the description and from the claims.

BRIEF DESCRIPTION OF THE DRAWINGS

FIGS. 3a-d are a set of diagrams showing that HaploSeq allows for accurate, high-resolution, and chromosome-span reconstruction of haplotypes: (a) Diagram of Hi-C reads (upper and lower bars) arising from the 129 allele that span ~30 Mb total of chromosome 18 and are used to link the variants into a single chromosome span haplotype; (b) Table of the results of Hi-C based haplotype phasing in CASTxJ129 system; (c) Comparison of haplotype phasing methods for generating complete haplotypes by simulation; (d) Analysis of the adjusted span (AS) of the haplotype phasing.

FIGS. 4a-d are a set of diagrams showing Haplotype reconstruction in human GM12878 cells using HaploSeq: (a) Diagram demonstrating the differences in variant frequency between mice (CASTx129) and humans (GM12878) over the Hoxd13/HOXD13 gene; (b) Table depicting the completeness ("% Chr Spanned in MVP block"), resolution ("% Variants Phased in MVP block"), and accuracy ("% Accuracy of variants phased in MVP block") of haplotype reconstruction using HaploSeq analysis in a low variant density scenario in CASTxJ129 system; (c) Table of results of the HaploSeq based haplotype reconstruction in GM12878 cells; (d) Hi-C generated seed haplotypes span the centromere of metacentric chromosomes.

FIGS. 5a-d are a set of diagrams showing that HaploSeq analysis coupled with local conditional phasing permits high resolution haplotype reconstruction in humans: (a) Diagram depicting ability to perform local conditional phasing; (b) Table demonstrating the resolution of haplotype phasing using HaploSeq after local conditional phasing along with overall accuracy in GM12878 cells; (c) Plot demonstrating the ability to achieve chromosome-span seed haplotype (MVP block) at varying parameters of read length and coverage, (d) Plot showing the ability of different combinations of read length and coverage to generate high-resolution seed haplotypes.

DETAILED DESCRIPTION OF THE INVENTION

Rapid advances in high-throughput DNA sequencing technologies are accelerating the pace of research into personalized medicine. While methods for variant discovery and genotyping from whole genome sequencing (WGS) datasets have been well established, linking variants on a chromosome together into a single haplotype remains a challenge.

Whole-Genome Haplotyping and Reconstruction

This invention provides a novel approach for haplotyping, which includes a proximity-ligation and DNA sequencing technique with a probabilistic algorithm for haplotype assembly (Dekker et al., Science 295, 1306-1311 (2002); Lieberman-Aiden et al., Science 326, 289-293 (2009); Kalhor et al., Nature Biotechnology 30, 90-98 (2012); and Bansal et al., Bioinformatics 24, i153-159 (2008)). The approach, termed "HaploSeq" for Haplotyping using Proximity-Ligation and Sequencing, reconstructs complete haplotypes or targeted haplotypes by utilizing proximity-ligation and DNA shotgun sequencing. As disclosed herein, HaploSeq has been experimentally validated in a hybrid mouse embryonic stem cell line and a human lymphoblastoid cell line in which the complete haplotypes are known a priori. It is demonstrated here that with HaploSeq, chromosome-span haplotype reconstruction can be achieved with over 95% of alleles linked at an accuracy of ~99.5% in mouse. In the human cell line, HaploSeq is coupled with local conditional phasing to obtain chromosome-span haplotypes at ~81% resolution with an accuracy of ~98% using just 17×coverage of genome sequencing. These results establish the utility of proximity-ligation and sequencing for haplotyping in human populations.

Figure 1A:
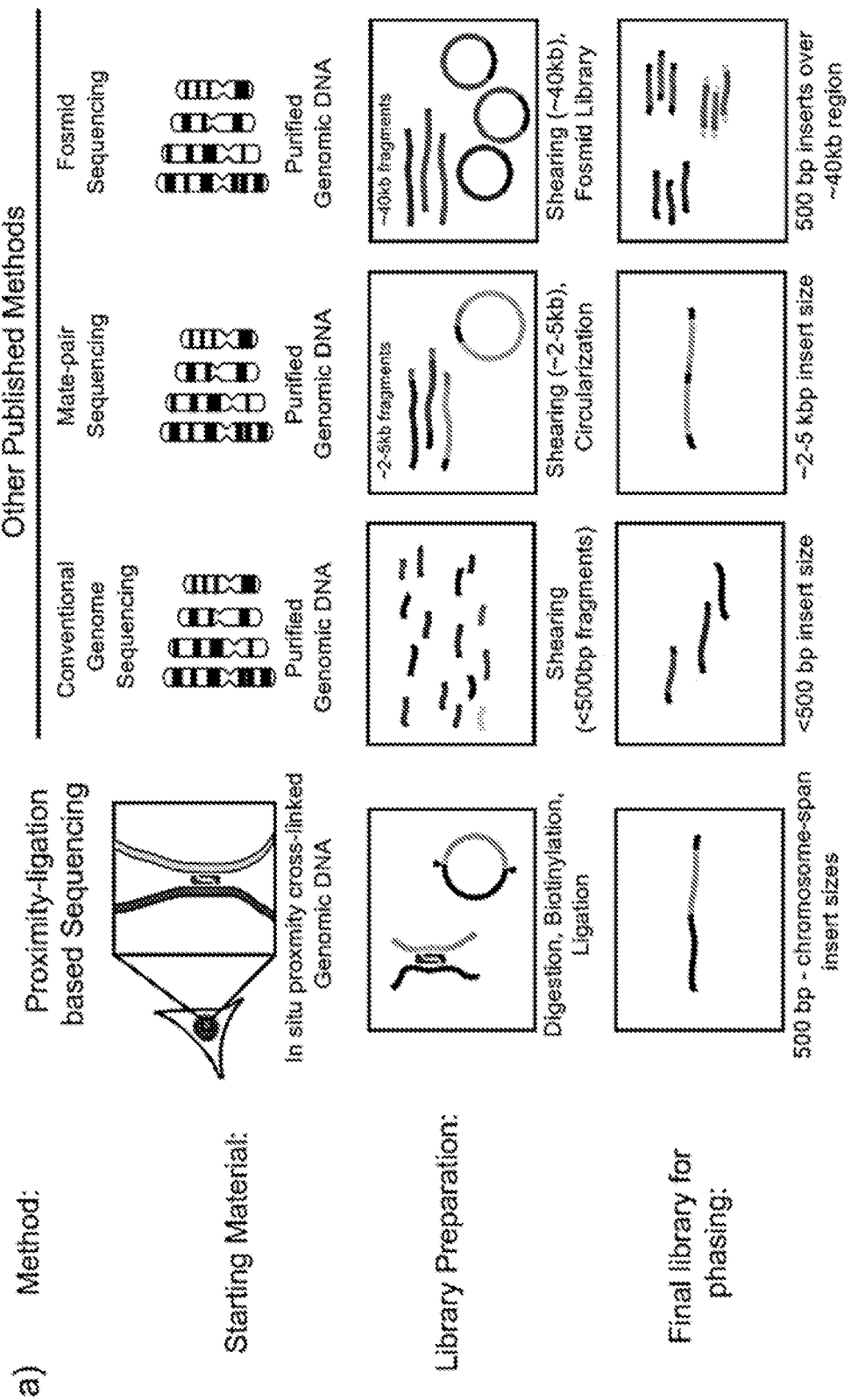
FIGS. 1*a-c* are a set of diagrams showing comparison of HaploSeq with other methods for reconstructing haplotypes of an organism: (a) Diagram outlining several methods used to phase haplotypes; (b) Frequency distributions of insert sizes from conventional whole genome sequencing (WGS), mate-pair and Hi-C; (c) Diagram illustrating the role of proximity-ligation reads in building chromosome span haplotypes.

An embodiment of the HaploSeq method of this invention is shown in FIG. 1. Briefly, FIG. 1a depicts comparison of HaploSeq with other methods for reconstructing haplotypes of an individual. The diagram outlines several methods used to phase haplotypes. Unlike previous methods, proximity-ligation links distal DNA fragments that are spatially close. These are then isolated from cells and sequenced.

Figures 1B, 1C:
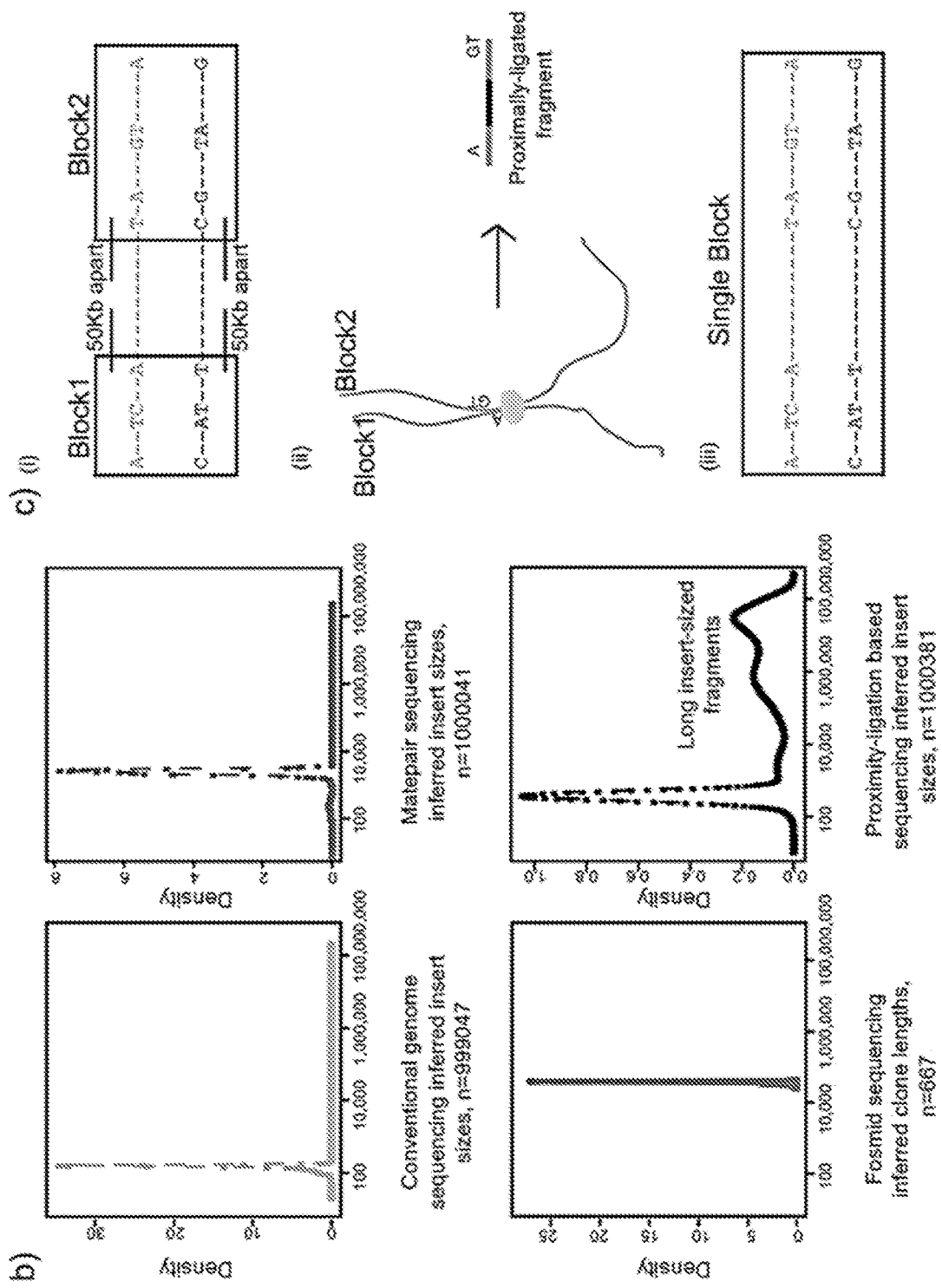

FIG. 1b shows frequency distributions of insert sizes from conventional WGS, mate-pair (Gnerre, S. et al. Proceedings of the National Academy of Sciences of the United States of America 108, 1513-1518 (2011)) and Hi-C. The x-axis is in base-pairs ($\log_{10}$ scale). Plots represent random subset of data points taken from previously published for GM12878 cells across chromosomes 1-22. In the case of fosmids (Kidd et al., Nature 453, 56-64 (2008)), size distribution of the clones inferred after alignment is shown. The Hi-C insert sizes are derived from libraries generated by the inventors' laboratory. Insert and clone sizes are correlated with the ability to reconstruct longer haplotypes. Among these methods, only proximity-ligation based Hi-C generates abundant long fragments.

FIG. 1c illustrates the role of proximity-ligation reads in building chromosome span haplotypes. The top and bottom sequences represent regions of two homologous chromosomes, where "-" represents no variability and nucleotides represent heterozygous SNPs. Heterozygous SNPs and indels can be used to distinguish the homologous chromosomes. Local haplotype blocks ("block 1" and "block 2") can be built from short insert sequencing reads (i), similar to what occurs in conventional WGS or mate pair sequencing. Given the distance between variants, these small haplotype blocks remain un-phased in relation to each other. Distally located regions in terms of linear sequence can be brought in close proximity in situ (ii). These linkages will be preserved by proximity-ligation. The large insert-size proximity-ligation sequencing reads help consolidate smaller haplotype blocks into a single chromosome span haplotype (iii).

The Hi-C techniques are known in the art and the related protocols can be found in US20130096009 and Lieberman-Aiden et al., Science 326, 289-293 (2009), the contents of which are incorporated by reference. In one embodiment, the Hi-C method comprises purifying ligation products followed by massively parallel sequencing. In one embodiment, a Hi-C method allows unbiased identification of chromatin interactions across an entire genome. In one embodiment, the method may comprise steps including, but not limited to, crosslinking cells with formaldehyde; digesting DNA with a restriction enzyme that leaves a 5'-overhang; filling the 5'-overhang that includes a biotinylated residue; and ligating blunt-end fragments under dilute conditions wherein ligation events between the cross-linked DNA fragments are favored. In one embodiment, the method may result in a DNA sample containing ligation products consisting of fragments that were originally in close spatial proximity in the nucleus, marked with the biotin residue at the junction. In one embodiment, the method further comprises creating a library (i.e., for example, a Hi-C library). In one embodiment, the library is created by shearing the DNA and selecting the biotin-containing fragments with streptavidin beads. In one embodiment, the library is then analyzed using massively parallel DNA sequencing, producing a catalog of interacting fragments. See, FIG. 1a.

Figure 2A:
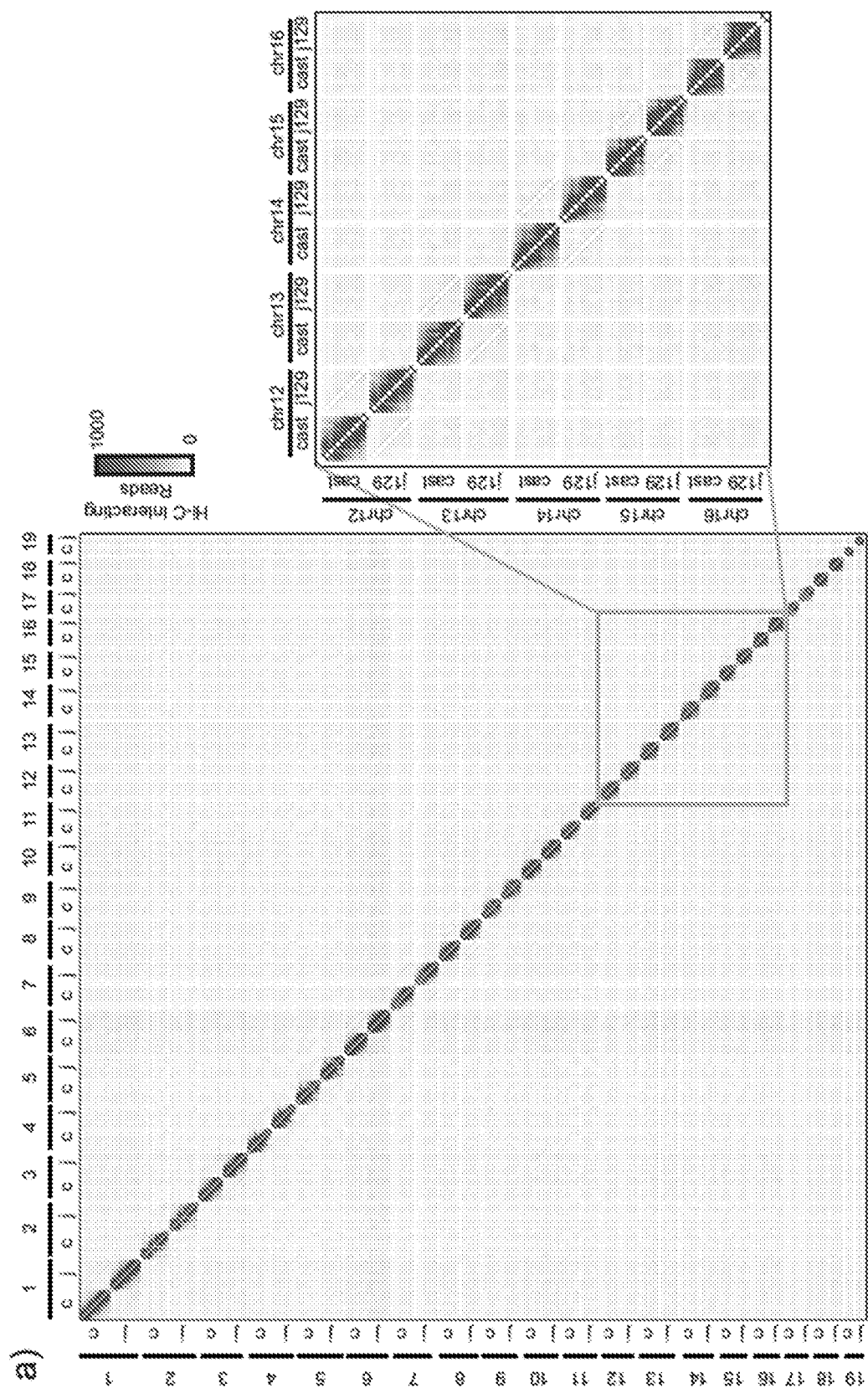
FIGS. 2*a-c* are a set of diagrams showing that proximity-ligation products are predominantly intra-haplotype; (a) Whole genome interaction frequency heat map; (b) Interaction frequencies ($\log_{10}$ scale) between any two fragments as a function of linear distance; (c) Comparison of the h-transr interaction probability as a function of insert size.
Figures 2B, 2C:
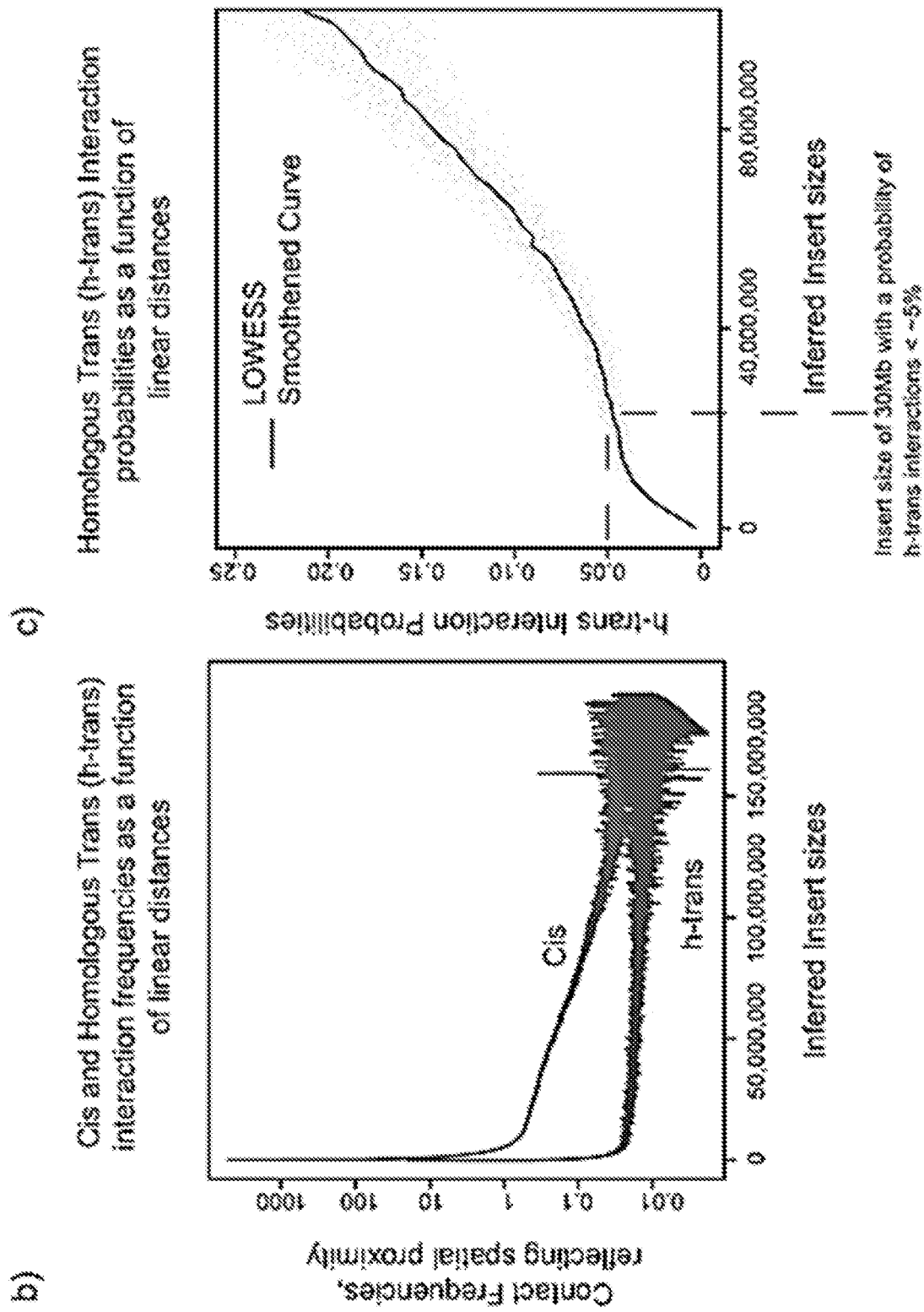

As disclosed herein and shown in FIG. 2, proximity-ligation products obtained by the method of this invention are predominantly intra-haplotype. To that end, FIG. 2a shows a whole genome interaction frequency heat map. Hi-C reads originating from the CAST ("c") or J129 ("j") genome were distinguished based on the known haplotype structures of the parental strains. The frequency of interactions between each allele of each chromosome was calculated using 10 Mb bin size. The CAST or J129 allele of each chromosome primarily interacts in cis, confirming that the chromosomes territories seen in Hi-C data occur for individual alleles. Inset shows a magnified view of the CAST and J129 allele for chromosomes 12 through 16. Furthermore, FIG. 2b shows the interaction frequencies ($\log_{10}$ scale) between any two fragments as a function of linear distance. From a prioiri haplotype information, read-pairs are distinguished as interacting in cis (top) and in h-trans (bottom). The interaction frequency in cis can be several orders of magnitude more frequent than in h-trans. Notably, the frequency of interactions in cis approaches that of in h-trans at large genomic distances (>100 Mbp) and <2% overall h-trans interactions were observed. Plot generated using data from chromosomes 1-19 in CASTxJ129 system. Finally, FIG. 2c shows comparison of the h-trans interaction probability as a function of insert size. Plot was generated using data from chromosomes 1-19 in CASTxJ129 system. LOWESS fit was performed at 2% smoothing. Below 30 Mb, the probability of a read being an h-trans interaction is ≤5% (dashed line). Therefore, this cutoff is used as a maximum insert size for further analysis.

Figure 3A:
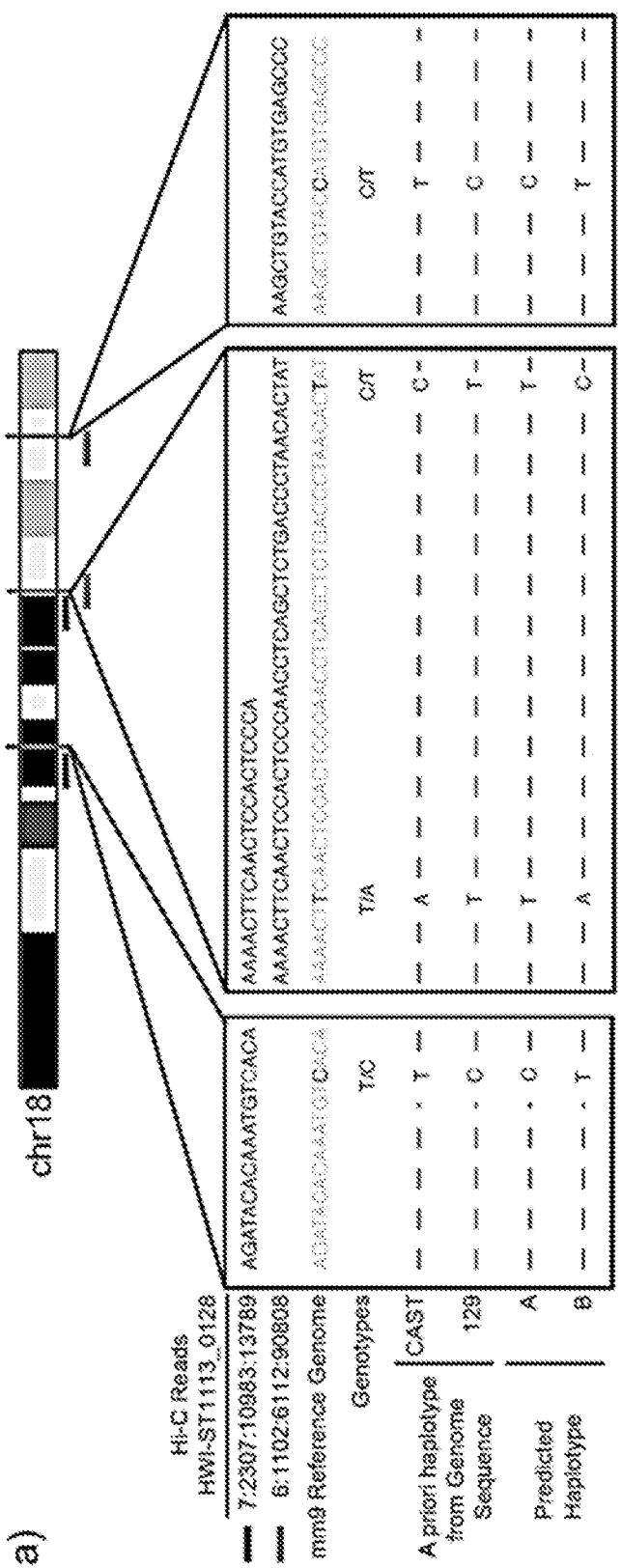

The HaploSeq approach of this invention allows for accurate, high-resolution, and chromosome-span reconstruction of haplotypes. FIG. 3a shows a diagram of Hi-C reads arising from the 129 allele that span ~30 Mb total of chromosome 18 and are used to link the variants into a single chromosome span haplotype. The sequence of the Hi-C reads is shown in black text with the variant locations in red and underlined. The sequence of the reference genome is in gray. A priori CAST and J129 haplotypes for each genotype were used at the variant locations as well as the predicted haplotype based on the Hi-C data. At these four bases, Hi-C generates a perfect match in terms of the identification of the known haplotype structure. HapCUT can then use these heterozygous variants as nodes and such overlapping reads as edges to form graph structures.

The table in FIG. 3b shows results of Hi-C based haplotype phasing in CASTxJ129 system. The "Phasable Span of Chr" column lists the numbers of phasable bases (the base-pair difference between first and last heterozygous variant). Listed in the "Variant spanned in MVP block" column is the total number of heterozygous variants spanned by the MVP block per chromosome, which is an alternative measure for completeness and is used as a denominator for estimating resolution. Listed in the "% Chr Spanned in MVP block" column are the percentages of phasable bases spanned by the predicted haplotype. Listed in the "% Variants Phased in MVP block" column are the percentages of all heterozygous variants phased among the variants spanned in the MVP block. Listed in the last column is the accuracy for each of the phased heterozygous variants. For each chromosome, the inventors generated complete (>99.9% of bases spanned), high-resolution (>95% of het. variants phased), and accurate (>99.5% correctly phased het. variants) haplotypes.

Figure 3D:
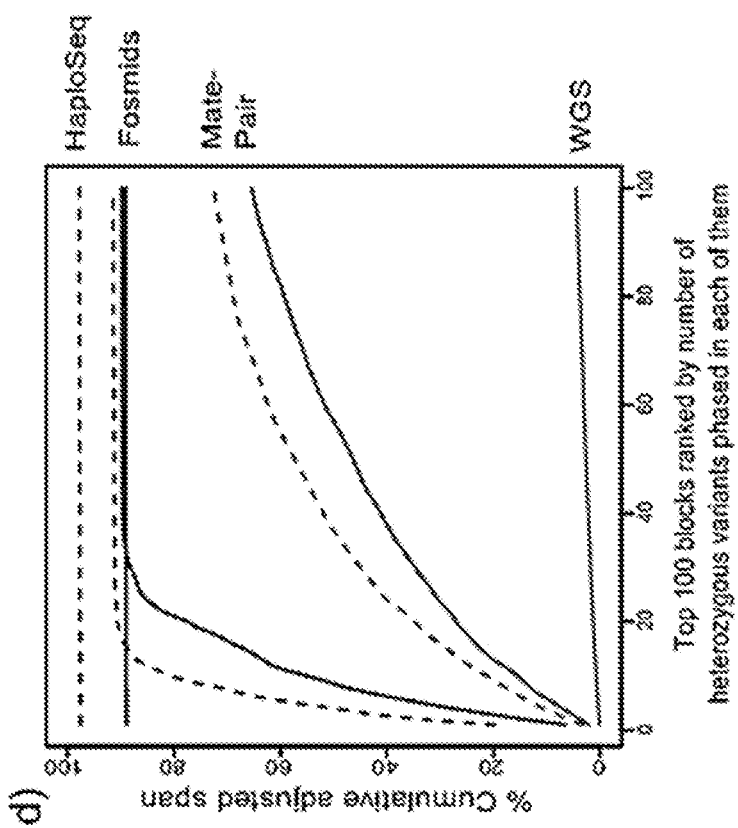
Figure 3C:
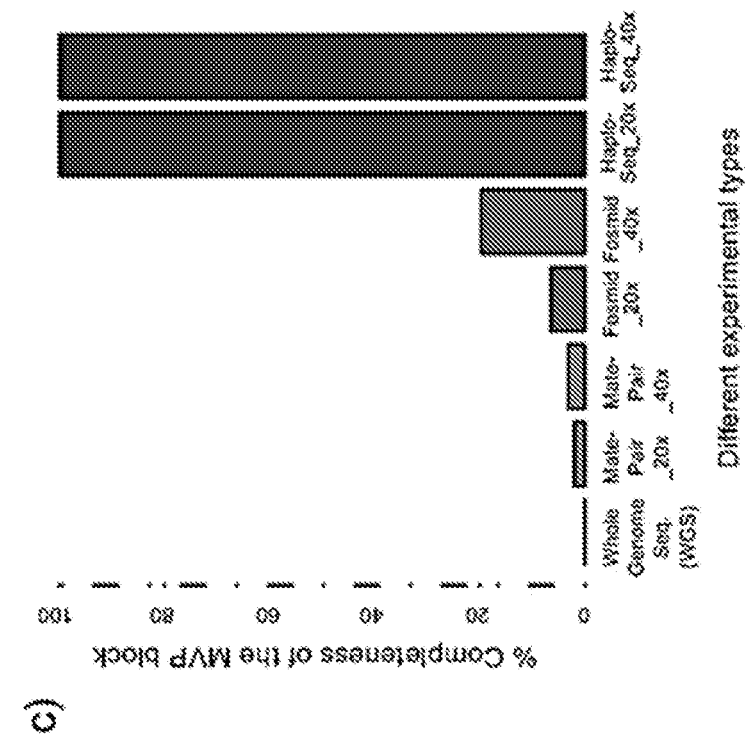

FIG. 3c further shows the comparison of haplotype phasing methods for generating complete haplotypes by simulation. The inventors simulated 75 base-pairs paired-end sequencing data (chromosome 19) of conventional shotgun sequencing (mean=400, sd=100), mate pair (mean=4500, sd=200) and fosmids (mean=35000, sd=2500) at 20×coverage. While the first read was randomly placed in the genome, the second read was chosen based on the above-mentioned normal distribution parameters. The inventors sub-sampled the CASTx129 data to generate 20×Hi-C fragments that were used for HaploSeq analysis. Y-axis represents the span of MVP block as a function of phasable span of chromosome 19. The MVP block in HaploSeq spans whole chromosome, whereas other methods MVP block spans only a fraction of the chromosome. The inventors also combined 20×sequencing coverage for each method with 20×conventional WGS data for a total of 40×coverage to compare methods at a higher coverage.

FIG. 3d shows an analysis of the adjusted span (AS) of the haplotype phasing. The AS is defined as the product of span and fraction of heterozygous variants phased in that block. Haplotype blocks were ranked by number of heterozygous variants phased in each block (x-axis is ranking) and the cumulative AS over the whole chromosome is represented on the y-axis. In the case of HaploSeq, the MVP block alone spans 100% of chromosome and contains 90% of variants phased. In other methods, percent phasing increased cumulatively as the inventors include non-MVP blocks. Dashed lines represent increased coverage at 40× by combining with WGS data as discussed above.

The HaploSeq approach of this invention also allows one to perform haplotype reconstruction in human cells, such as GM12878 cells. To that end, FIG. 4a demonstrates the differences in variant frequency between mice (CASTx129) and humans (GM12878) over the Hoxd13/HOXD13 gene. Also shown is the Hi-C read coverage ($\log_{10}$ scale) over these loci. Hi-C reads are more likely to contain variants in the high SNP density (mouse) case (shown as "SNP-covering reads"). This in turn allows these variants to be more readily connected to the MVP block. In the low variant density scenario (human), this is not the case, and as a result there are "gaps" where variants remain unphased relative to the MVP block.

In addition, the table in FIG. 4b shows the completeness ("% Chr Spanned in MVP block"), resolution ("% Variants Phased in MVP block"), and accuracy ("% Accuracy of variants phased in MVP block") of haplotype reconstruction using HaploSeq analysis in a low variant density scenario in CASTxJ129 system. Variants were sub-sampled in the CASTx129 genome to have a heterozygous variant every 1500 bases and phasing was performed as described above. The inventors continued to generate haplotypes that are complete (>99% chromosome span) and accurate (>99% accuracy). However, there is a reduction in the resolution of the variants phased (~32%) in the low variant density scenario. Numbers are rounded off to three decimals.

Also, the table in FIG. 4c summarizes results of the HaploSeq based haplotype reconstruction in GM12878 cells. The results show completeness ("% Chr Spanned in MVP block") and resolution ("% Variants Phased in MVP block"). The inventors were able to generate chromosome-span haplotypes (>99%), albeit at a lower resolution (~22%). In GM12878 cells, the inventors generated ~17× coverage when compared to ~30× in CASTxJ129 system. Therefore, the inventors observed a lower resolution (22%) when compared to low-density CASTxJ129 (32%). Numbers are rounded off to three decimals.

Figure 4A:
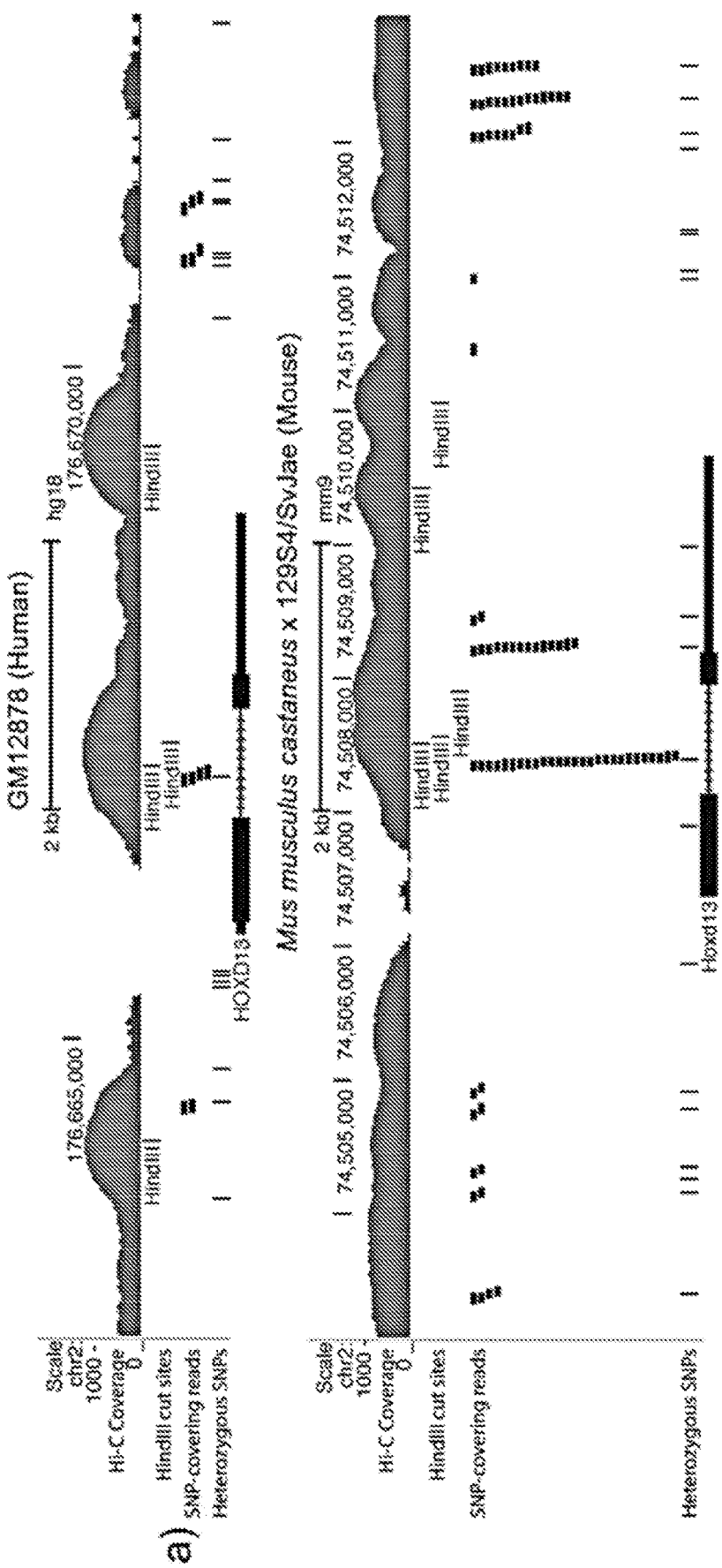
Figure 4D:
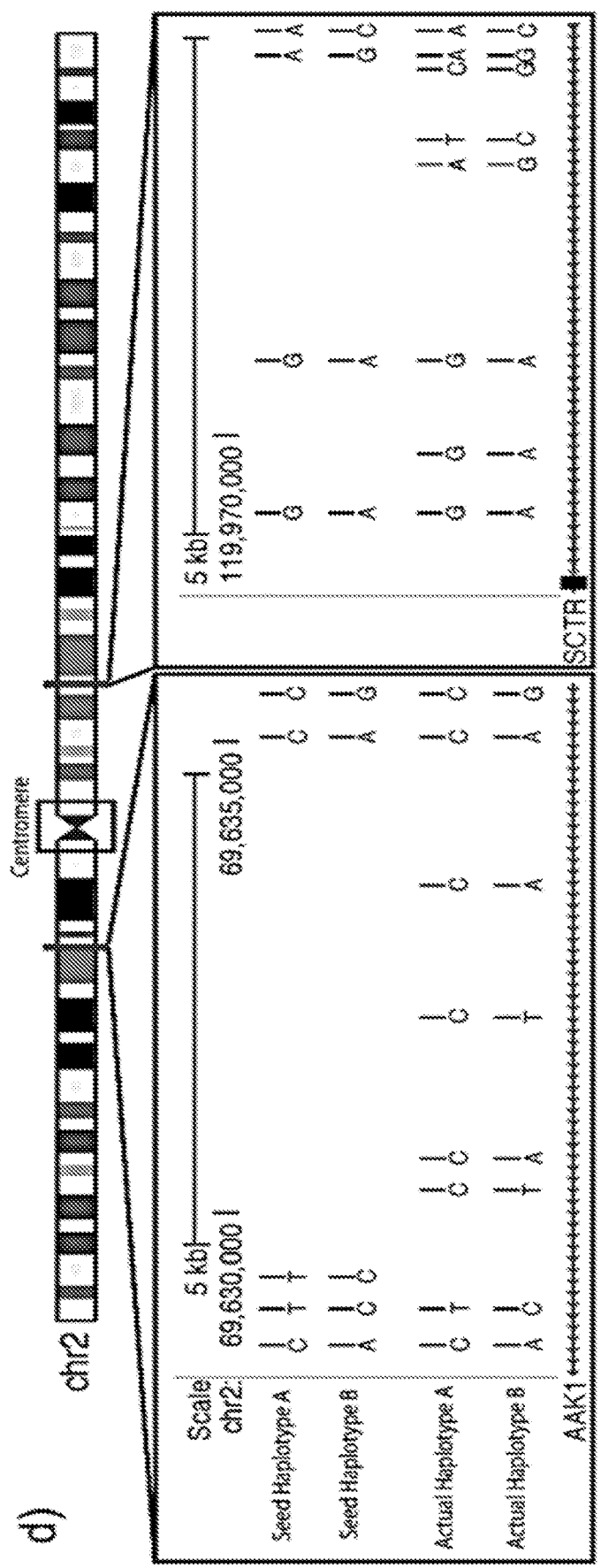

As shown in FIG. 4d, the method of this invention allows one to generate seed haplotypes that span the centromere of metacentric chromosomes. Shown are two regions on either side of the centromere of chromosome 2. The two Hi-C generated seed haplotypes are arbitrarily designated as "A" and "B." The actual haplotypes of the GM12878 individual learned from trio sequencing are shown below designated arbitrarily as "A" and "13." The Hi-C generated seed haplotypes match the actual haplotypes on both sides of the centromere. Of note, some variants in the actual haplotype remain unphased, thus contributing to the "gaps" in the seed haplotype. In addition, the actual haplotypes do not contain all variants as trio-sequencing was performed at low depth, therefore the seed haplotype contains some phased variants not in the actual haplotype (see the third variant in the AAK1 region for example).

Figures 5A, 5B:
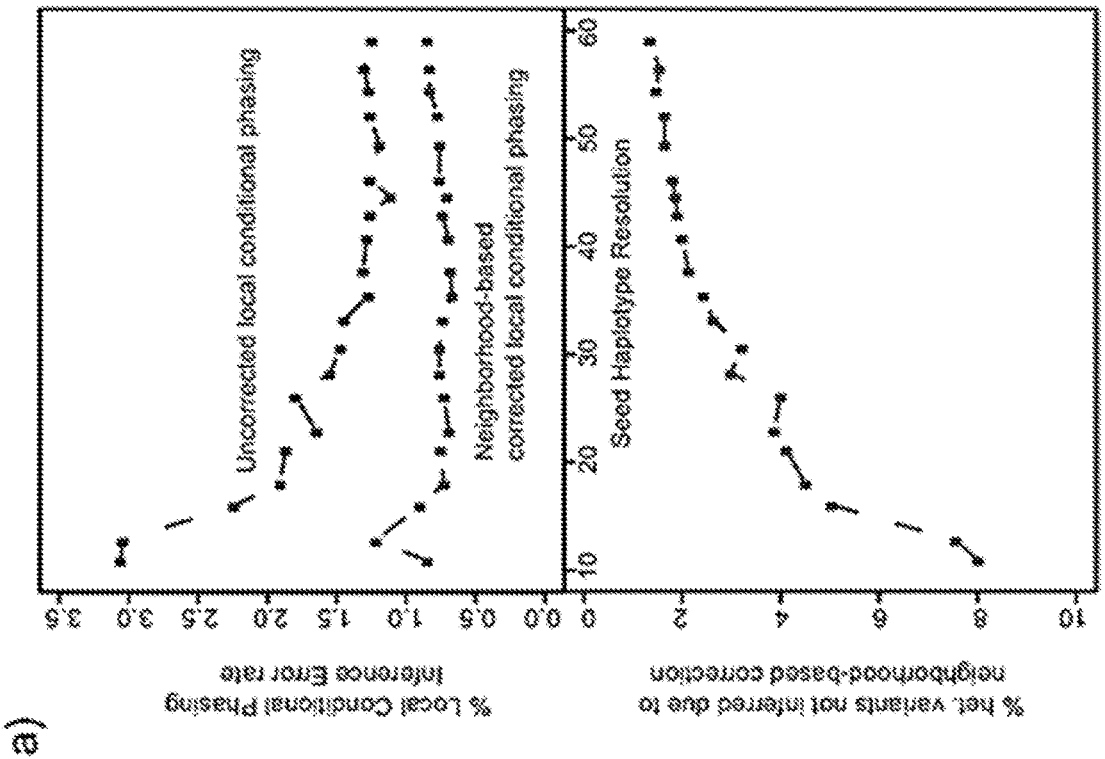

The HaploSeq analysis can be used in conjunction with other techniques, such as local conditional phasing to permit high resolution haplotype reconstruction in humans. FIG. 5a) shows the ability to perform local conditional phasing. The x-axis is the chromosome span seed haplotypes resolution generated by simulation. The top panel shows the error rates of local conditional phasing using both an uncorrected (upper) and neighborhood corrected phasing (lower, window size=3). Because of neighborhood correction, some variants cannot be locally inferred. The bottom panel shows the percentage of variants that remain unphased due to neighborhood correction as a function of resolution. All simulations are done in GM12878 chromosome 1.

The table in FIG. 5b demonstrates the resolution of haplotype phasing using HaploSeq after local conditional phasing along with overall accuracy in GM12878 cells. With the local conditional phasing, the inventors increased resolution from ~22% to ~81% on average. The table also depicts resolution lost due to neighborhood correction (NC), which is on average only ~3%. The inventors used a window size of 3 seed haplotype phased variants to check performance of local phasing. Apart from enhanced resolution, the inventors also obtained accurate haplotypes, with an overall accuracy ~98%. Accuracy here reflects error from MVP block of initial HaploSeq analysis and error from local conditional phasing. For some chromosomes, the accuracy was lower due to lower coverage (see Table 1 below).

The plot in FIG. 5c also demonstrates the ability to achieve chromosome-span seed haplotype (MVP block) at varying parameters of read length and coverage. In all cases, chromosome span seed haplotype can be obtained with ~15× usable coverage. All simulations are done in GM12878 chromosome 1. Similarly, the plot in FIG. 5d shows the ability of different combinations of read length and coverage to generate high-resolution seed haplotypes. In this instance, longer-read lengths contribute to a greater resolution of the Hi-C generated seed haplotypes. All simulations are done in GM12878 chromosome 1.

The inventors describe herein a novel strategy to reconstruct a chromosome-span haplotype for an organism. Compared to other haplotyping methods that reconstruct complete haplotypes from shotgun sequencing reads, the method disclosed herein can generate chromosome-span haplotypes (Fan et al., Nature Biotechnology 29, 51-57 (2011); Yang et al., Proceedings of the National Academy of Sciences of the United States of America 108, 12-17 (2011); and Ma et al., Nature Methods 7, 299-301 (2010)). This approach is most suitable for clinical and laboratory setting, since the reagents and equipment required for HaploSeq experiment are readily available. Further, the method is more apt than sperm cell genotyping based approach (Kirkness et al., Genome Research 23, 826-832 (2013)), as it can generate whole-genome haplotypes from intact cells of any individual or cell-line. HaploSeq is thus of great utility in personalized medicine. Determination of haplotypes in individuals allows the identification of novel haplotype-disease associations, some of which have already been identified on smaller scales (He et al., American Journal of Human Genetics 92, 667-680 (2013); Zeng et al., Genetic Epidemiology 28, 70-82 (2005); and Chapman et al., Human Heredity 56, 18-31 (2003)). In addition, complete haplotypes will be essential for understanding allelic biases in gene expression, which will contribute to genetic and epigenetic polymorphisms in the population and their phenotypic consequences at a molecular level (Gimelbrant et al., Science 318, 1136-1140 (2007); Kong et al., Nature 462, 868-874 (2009); and McDaniell et al., Science 328, 235-239 (2010)). Furthermore, HaploSeq can be used to identify genetic polymorphisms in cancer cells that either cause or are markers for resistance to cancer treatment drugs. Lastly, while the approach is exemplified for diploid cells in the examples below, experimental and computational improvements allow for haplotype reconstruction in cells with higher ploidy, such as cancer cells. This can aid in the understanding of the consequences of the genetic alterations that are frequently seen during oncogenesis.

Previously, proximity-ligation was used to study the spatial organization of chromosomes (Lieberman-Aiden et al., Science 326, 289-293 (2009)), but not haplotype determination at the whole genome level. As disclosed herein, it is also a valuable tool in studying the genetic makeup of an individual. As demonstrated herein, proximity-ligation based approaches can not only tell which cis-regulatory element is physically interacting with which target gene, but also which alleles of these are linked on the same chromosome. Proximity-ligation data can also be used for genotyping, on the same lines as WGS. Although variants far from restriction enzyme cut sites are less likely to be genotyped owing to biases from proximity-ligation approaches such as Hi-C, population based imputation (Browning et al., American Journal Of Human Genetics 81, 1084-1097 (2007)) of un-genotyped variants can be performed in supplement to achieve increased genotype calls. Because all this can be done using a single experiment, HaploSeq can be used as a general tool for whole genome analysis.

Targeted Haplotyping and Reconstruction

HaploSeq can also be used for targeted haplotyping of distinct regions. Once the ligation step is performed and a library of proximally-ligated fragments is obtained, custom-designed oligonucleotides, which may be immobilized on a solid surface, are introduced to the library in solution. These oligonucleotides "target" specific proximity-ligation fragments and hybridize to those proximity-ligation fragments. The proximity-ligation fragments that are hybridized to such oligonucleotides are isolated to provide new library. This library now contains a subset of proximally-ligated fragments that were captured by the custom oligonucleotides. These fragments are sequenced and assembled to generate directed haplotypes. This method is useful for the directed haplotyping of distinct regions. For example, directed haplotyping of the HLA region (also known as human major histocompatibility complex locus or human leukocyte antigen locus), which is about 3.5 Mb, can be performed by this method. Such directed haplotyping of the HLA region is useful in predicting outcomes for donor-host matching in organ transplantation.

Figure 9:
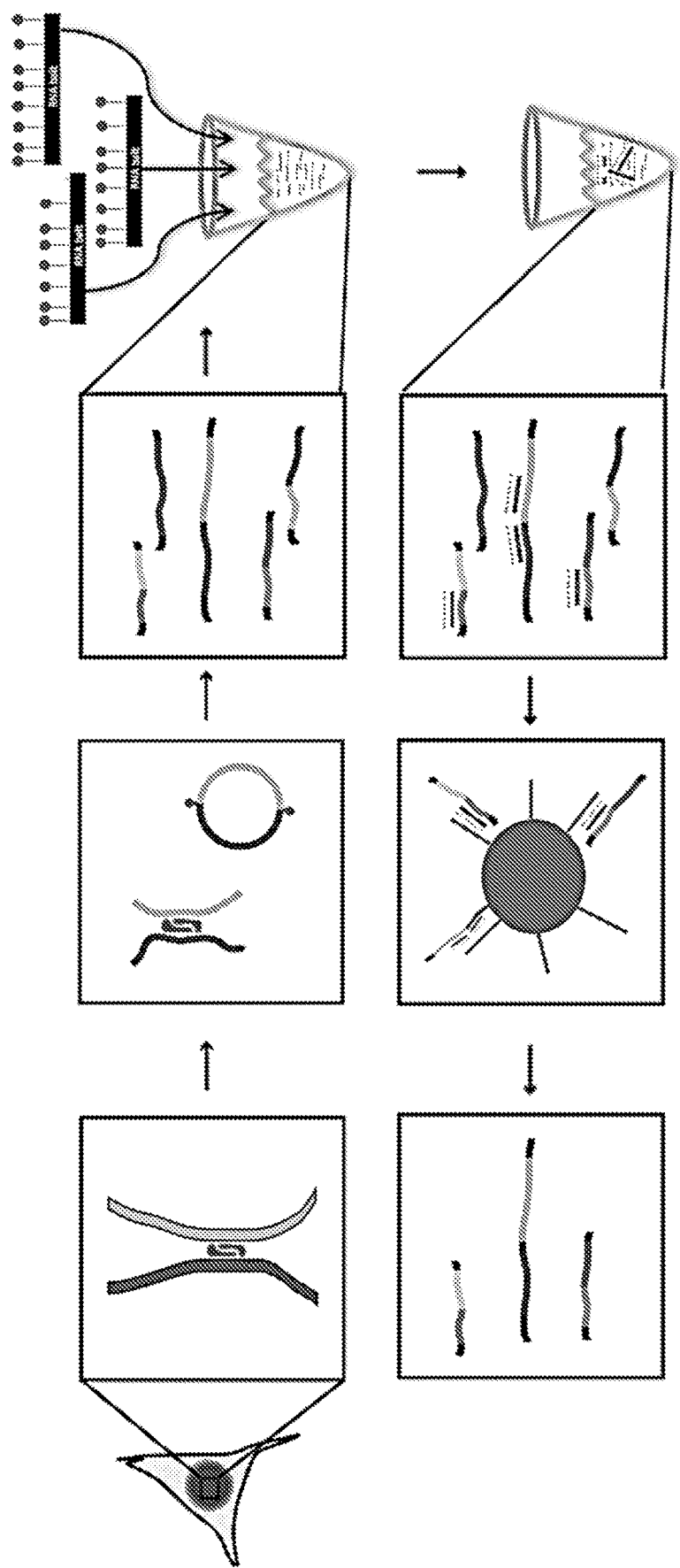
FIG. 9 is a diagram showing a Capture-HiC experimental scheme.

Shown in FIG. 9 is a schematic example for this targeted haplotyping. First, cells are cross-linked and fixed, thereby capturing the spatially proximal DNA element (top left). Then, the cells are digested with, e.g., HindIII and fragmented ends are filled in with a biotinylated nucleotide, followed by re-ligation of digested ends as performed in the Hi-C protocol (top middle). After PCR amplification of the Hi-C fragments, the final Hi-C library is composed of Hi-C di-tags that can be targeted by biotinylated RNA probes which have been designed to capture specific Hi-C fragments (top right). Then, using oligonucleotide capture technology (OCT), one can perform solution hybridization of the RNA probes to the Hi-C library. Here, some Hi-C fragments will have been targeted by two RNA probes, while others only one, and all non-targeted sequences will be unbound by RNA probe (bottom right). Next, streptavidin-coated beads are used to bind the biotinylated RNA:DNA duplexes (bottom middle), thereby extracting the targeted Hi-C fragments from the Hi-C library, and creating the Capture-HiC library. The bead-bound Hi-C library then is PCR amplified, purified, and subject to next-generation sequencing (bottom left).

Figure 10A:
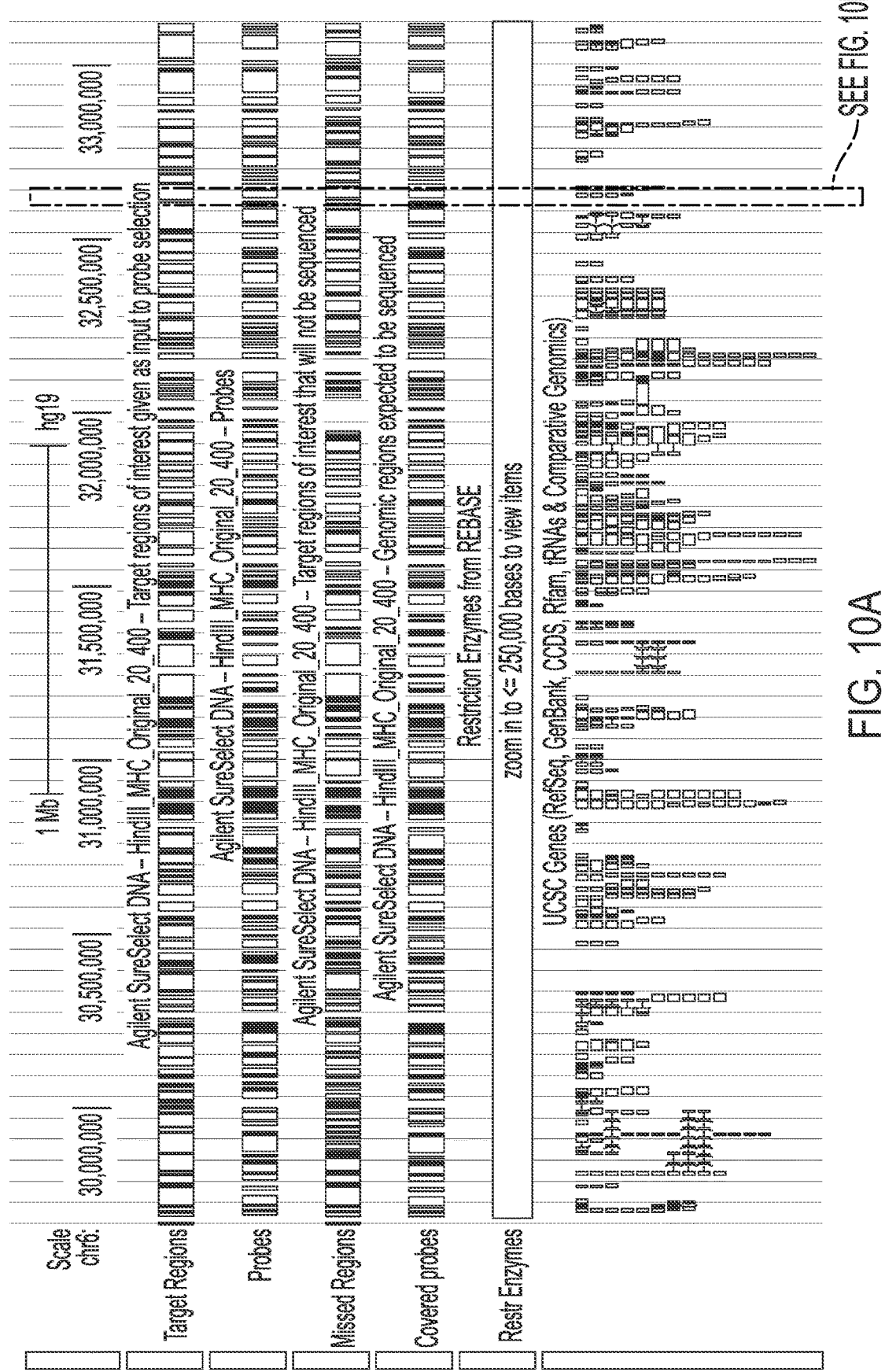
FIGS. 10a-b show a Capture-HiC probe design: (a) a UCSC Genome Browser shot of the HLA locus in humans (hg19) and (b) a Zoom-in UCSC Genome Browser shot of the HLA-DQB1 gene to demonstrate the probe targeting approach.
Figure 10B:
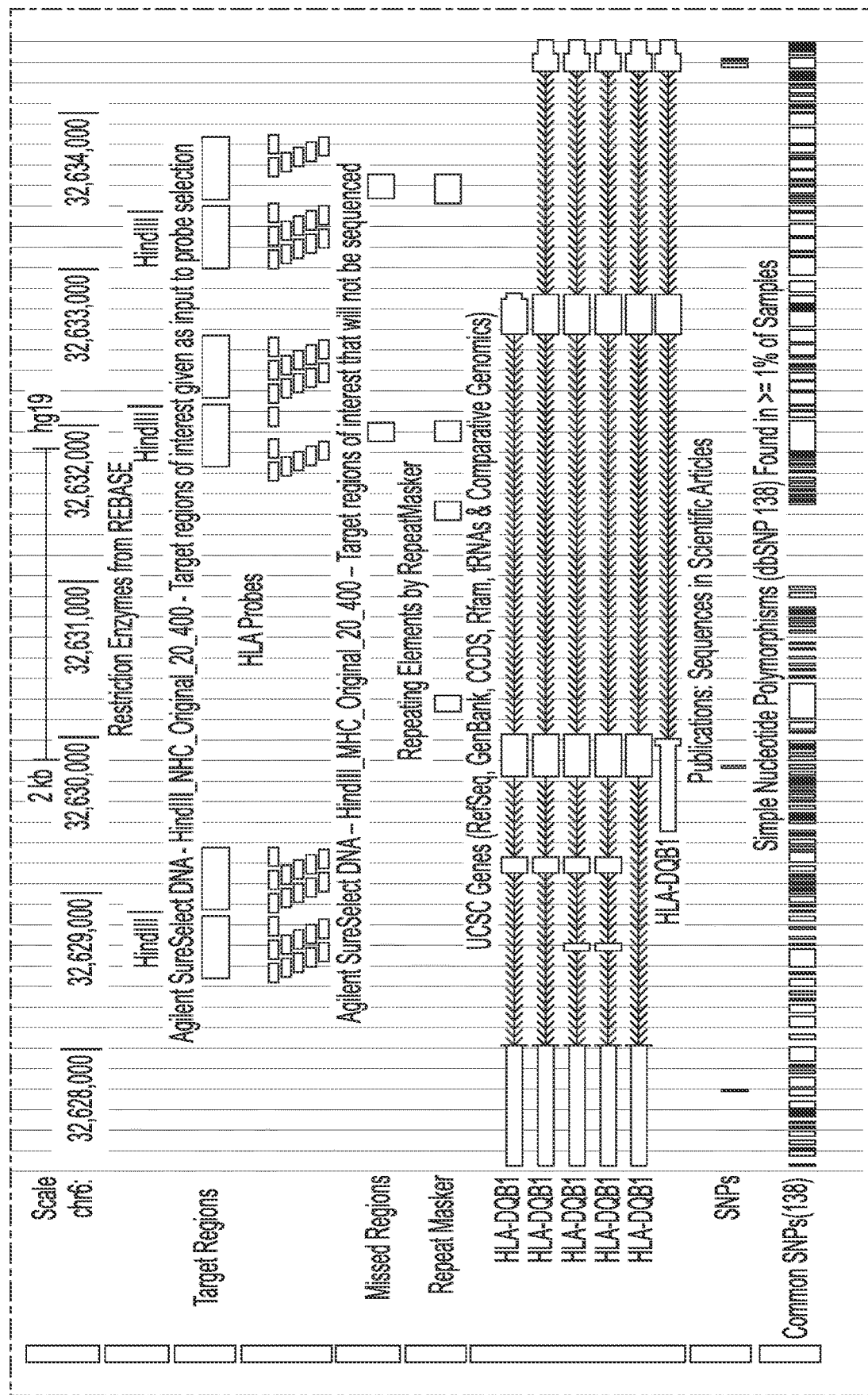

In the examples below, the above-described approach was used for haplotyping the human HLA region, which is about 3.5 Mb. Shown in FIG. 10 is a Capture-HiC probe design used in the examples. Probe sequences were first computationally generated using the SureDesign software suite (Agilent). Shown in FIG. 10a is a UCSC Genome Browser shot of the HLA locus in humans (hg19). FIG. 10b shows a Zoom-in UCSC Genome Browser shot of the HLA-DQB1 gene to demonstrate the probe targeting approach. In that case, the inventors targeted the +/−400 bp adjacent to the restriction enzyme cut sites used to prepare the Hi-C library, in this case HindIII ("Targeted Regions" track). For the targeted regions, probes were designed at 4× tiling density, which aims to have each nucleotide of target sequence covered by up to 4 probe sequences. Also note that the probes do not overlap the HindIII cut site itself ("HLA Probes" track). It was also elected to not target any sequence within the targeted region that was called to contain repetitive sequences by RepeatMasker ("Missed Regions" and "RepeatMasker" track).

The targeted haplotyping approaches discussed herein, e.g., the Capture-HiC approach, present an opportunity to phase the entire HLA locus into a single haplotype block, enabling better predictive HLA type matching in cell and organ transplantation procedures. Several studies have uncovered numerous disease-associated non-coding variants associated with specific HLA genes or alleles (Trowsdale et al., *Annual Review Of Genomics And Human Genetics* 14, 301-323, (2013) and Trowsdale, *Immunology letters* 137, 1-8, (2011)). Therefore, by delineating a single haplotype structure of HLA, one can systematically deconvolute the role of genetic variation on HLA linked diseases and phenotypes.

As demonstrated herein, the Capture-HiC approach generally preserves the chromatin interaction measurements detected by conventional Hi-C experiments. Therefore, Capture-HiC can be used as a method to obtain long-range interactions at specific loci. For example, utilizing Capture-HiC can reveal haplotype-resolved long-range interaction mechanisms behind genome imprinting. While several groups currently use the 4C and 5C technologies to study targeted chromatin interactions (Simonis et al., *Nature Genetics* 38, 1348-1354, (2006), and Dostie et al. *Genome Research* 16, 1299-1309, (2006)), Capture-HiC offers a more flexible methodology. In particular, 4C is limited to analysis of interactions with a single viewpoint and 5C is limited by complex primer design, limited throughput, and analysis of only continuous genomic regions. Alternatively, Capture-HiC can be applied to detect interactions of thousands of viewpoints in a single experiment, and is capable of retrieving regional and customized 3D interaction frequencies in an unbiased fashion. Specifically, Capture-HiC offers the capability to be tailored to capture any interspersed genomic element given the element's relative proximity to the restriction enzyme cut site, and therefore applicable to generalized cases. For example, by applying Capture-HiC to genome-wide promoters or other genomic elements, one can generate maps of 3D regulatory interactions genome-wide at unprecedented resolution and relatively low cost.

The Hi-C protocol has recently been demonstrated to be useful in assembling genomes de novo. (Burton et al. Nat Biotechnol 31, 1119-1125, (2013) and Kaplan et al. Nat Biotechnol 31, 1143-1147, (2013)) As Capture-HiC obtains high-quality chromatin interaction datasets, similar to Hi-C, this methodology can be used to generate diploid assembly of complex regions, such as the T-cell Receptor beta (Trcb) locus (Spicuglia et al., Seminars in Immunology 22, 330-336, (2010)), of human and other large genomes. Furthermore, diploid assembly of the highly heterozygous HLA locus performed in a population scale can allow detection of novel structural variations and enable precise delineating of human migration patterns as well as perform association studies to discover personalized medications for various disease states. Similarly, Hi-C has also recently been used in metagenomics studies to deconvolute the species present in complex microbiome mixtures (Beitel et al., PeerJ, doi: 10.7287/peerj.preprints.260v1 (2014) and Burton et al., Species-Level Deconvolution of Metagenome Assemblies with Hi-C-Based Contact Probability Maps. G3, doi:10.1534/g3.114.011825 (2014). With the advent of Capture-HiC, one can capture distinct loci that are informative and discriminative enough to delineate species mixtures based on the captured Hi-C fragments. Taken together, Capture-HiC and its application for targeted phasing as well as the other applications disclosed herein enable new avenues in personalized clinical genomics as well as biomedical research.

The term "marker" or "junction marker" as used herein, refers to any compound or chemical moiety that is capable of being incorporated within a nucleic acid and can provide a basis for selective purification. For example, a marker may include, but not be limited to, a labeled nucleotide linker, a labeled and/or modified nucleotide, nick translation, primer linkers, or tagged linkers. The term "labeled nucleotide linker" refers to a type of marker comprising any nucleic acid sequence comprising a label that may be incorporated (i.e., for example, ligated) into another nucleic acid sequence. For example, the label may serve to selectively purify the nucleic acid sequence (i.e., for example, by affinity chromatography). Such a label may include, but is not limited to, a biotin label, a histidine label (i.e., 6His), or a FLAG label.

The term "labeled nucleotide," "labeled base," or "modified base" refers to a marker comprising any nucleotide base attached to a marker, wherein the marker comprises a specific moiety having a unique affinity for a ligand. Alternatively, a binding partner may have affinity for the junction marker. In some examples, the marker includes, but is not limited to, a biotin marker, a histidine marker (i.e., 6His), or a FLAG marker. For example, dATP-Biotin may be considered a labeled nucleotide. In some examples, a fragmented nucleic acid sequence may undergo blunting with a labeled nucleotide followed by blunt-end ligation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "fragments" refers to any nucleic acid sequence that is shorter than the sequence from which it is derived. Fragments can be of any size, ranging from several megabases and/or kilobases to only a few nucleotides long. Experimental conditions can determine an expected fragment size, including but not limited to, restriction enzyme digestion, sonication, acid incubation, base incubation, microfluidization etc.

The term "chromosome" as used herein, refers to a naturally occurring nucleic acid sequence comprising a series of functional regions termed genes that usually encode proteins. Other functional regions may include microRNAs or long noncoding RNAs, or other regulatory elements. These proteins may have a biological function or they directly interact with the same or other chromosomes (i.e., for example, regulatory chromosomes).

The term "genomic region" or "region" refers to any defined length of a genome and/or chromosome. For example, a genomic region may refer to the association (i.e., for example, an interaction) between more than one chromosomes. Alternatively, a genomic region may refer to a complete chromosome or a partial chromosome. Further, a genomic region may refer to a specific nucleic acid sequence on a chromosome (i.e., for example, an open reading frame and/or a regulatory gene).

The term "fragmenting" refers to any process or method by which a compound or composition is separated into smaller units. For example, the separation may include, but is not limited to, enzymatic cleavage (i.e., for example, transposase-mediated fragmentation, restriction enzymes acting upon nucleic acids or protease enzymes acting on proteins), base hydrolysis, acid hydrolysis, or heat-induced thermal destabilization.

The term "heatmap" refers to any graphical representation of data where the values taken by a variable in a two-dimensional map are represented as colors. Heat maps have been widely used to represent the level of expression of many genes across a number of comparable samples (e.g. cells in different states, samples from different patients) as obtained from DNA microarrays.

The term "genome" refers to any set of chromosomes with the genes they contain. For example, a genome may include, but is not limited to, eukaryotic genomes and prokaryotic genomes.

The term "fixing," "fixation" or "fixed" refers to any method or process that immobilizes any and all cellular processes. A fixed cell, therefore, accurately maintains the spatial relationships between intracellular components at the time of fixation. Many chemicals are capable of providing fixation, including but not limited to, formaldehyde, formalin, or glutaraldehyde.

The term "crosslink," "crosslinking" or "crosslink" refers to any stable chemical association between two compounds, such that they may be further processed as a unit. Such stability may be based upon covalent and/or non-covalent bonding. For example, nucleic acids and/or proteins may be cross-linked by chemical agents (i.e., for example, a fixative) such that they maintain their spatial relationships during routine laboratory procedures (i.e., for example, extracting, washing, centrifugation etc.)

The term "join" refers to a unique linkage of two nucleic acid sequences by a junction marker. Such linkages may arise by processes including, but not limited to, fragmentation, filling in with marked nucleotides, and blunt end ligation. Such a join reflects the proximity of two genomic regions thereby providing evidence of a functional interaction. A join comprising a junction marker may be selectively purified in order to facilitate a sequencing analysis.

The term "ligated" as used herein, refers to any linkage of two nucleic acid sequences usually comprising a phosphodiester bond. The linkage is normally facilitated by the presence of a catalytic enzyme (i.e., for example, a ligase) in the presence of co-factor reagents and an energy source (i.e., for example, adenosine triphosphate (ATP)).

The term "restriction enzyme" refers to any protein that cleaves nucleic acid at a specific base pair sequence.

The term "selective purification" refers to any process or method by which a specific compound and/or complex may be removed from a mixture or composition. For example, such a process may be based upon affinity chromatography where the specific compound to be removed has a higher affinity for the chromatography substrate than the remainder of the mixture or composition. For example, nucleic acids labeled with biotin may be selectively purified from a mixture comprising nucleic acids not labeled with biotin by passing the mixture through a chromatography column comprising streptavidin.

The term "purified" or "isolated" refer to a nucleic acid composition that has been subjected to treatment (i.e., for example, fractionation) to remove various other components, and which composition substantially retains its expressed biological activity. Where the term "substantially purified" is used, this designation will refer to a composition in which the nucleic acid forms the major component of the composition, such as constituting about 50%, about 60%, about 70/o, about 80%, about 90%, about 95% or more of the composition (i.e., for example, weight/weight and/or weight/volume). The term "purified to homogeneity" is used to include compositions that have been purified to 'apparent homogeneity" such that there is single nucleic acid sequence (i.e., for example, based upon SDS-PAGE or HPLC analysis). A purified composition is not intended to mean that some trace impurities may remain. The term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" or "nucleotide sequence" refers to an oligonucleotide or polynucleotide, and fragments or portions thereof, and to DNA or RNA of genomic or synthetic origin which may be single-stranded or double-stranded, and represent the sense or antisense strand.

The term "an isolated nucleic acid" refers to any nucleic acid molecule that has been removed from its natural state (e.g., removed from a cell and is, in a preferred embodiment, free of other genomic nucleic acid).

The term "variant" of a nucleotide refers to novel nucleotide sequence which differs from a reference oligonucleotide by having deletions, insertions and substitutions. These may be detected using a variety of methods (e.g., sequencing, hybridization assays etc.). A "deletion" is defined as a change in either nucleotide or amino acid sequence in which one or more nucleotides or amino acid residues, respectively, are absent. An "insertion" or "addition" is that change in a nucleotide or amino acid sequence which has resulted in the addition of one or more nucleotides or amino acid residues. A "substitution" results from the replacement of one or more nucleotides or amino acids by different nucleotides or amino acids, respectively.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency.

The term "cancer treatment drugs" as used herein refers to all chemotherapeutic agents to which cancer cells can acquire chemoresistance, Examples include JAK/STAT inhibitors, P13 kinase inhibitors, mTOR inhibitors, ErbB inhibitors, topoisomerase inhibitors, and so forth.

EXAMPLES

Example 1 General Methods and Materials

This example describes general methods and materials used in Examples 2-9 below.

Cell Culture and Experimental Methods

The F1 Mus musculus castaneus×S129/SvJae (F123 line) were a gift from the laboratory of Edith Heard and have been described previously in Gribnau et al., Genes & Development 17, 759-773 (2003). These cells were grown in Knock-Out Serum Replacement containing mouse ES cell media: DM EM 85%, 15% KnockOut Serum Replacement (Invitrogen), penicillin/streptomycin, 1×Non-essential amino acids (GIBCO), 1×GlutaMax, 1000 U/mL LIF (MILLI-PORE), 0.4 mM β-mercaptoethanol. F123 mouse ES cells were initially cultured on 0.1% Gelatin-coated plates with mitomycin-C treated mouse embryonic fibroblasts (Millipore). Cells were passaged twice on 0.1% gelatin-coated feeder free plates before harvesting. GM12878 cells (CORIELL) were cultured in suspension in 85% RPMI media supplemental with 15% fetal bovine serum and 1×penicillin/streptomycin.

Cells were harvested either in suspension (GM12878) or after trypsin treatment (F123 mouse ES cells). Formaldehyde fixation and Hi-C experiments were performed as previously described in Lieberman-Aiden et al., Science 326, 289-293 (2009).

Genotyping

Variant calls and genotypes for GM12878 were downloaded from DePristo et al., Nature Genetics 43, 491-498 (2011) and these were used for haplotype reconstruction. Phasing Information for GM12878 was downloaded from 1000 genomes project (Genomes Project, C. et al., Nature 467, 1061-1073 (2010)). The phasing of GM12878 by the 1000 genomes project utilized low coverage sequencing and so covers only ~65% of heterozygous variants genotyped (DePristo et al., Nature Genetics 43, 491-498 (2011)) in this individual's genome. Of note, "GM12878" is the name of the lymphoblastoid cell line while "NA12878" is the identifier for the individual from whom this cell line was derived. GM12878 was used throughout the examples here for the sake of consistency and clarity.

For generating genotype calls for the hybrid CASTxJ129 cells, parental genome sequencing data was downloaded from publicly available databases. For Mus musculus castaneus, the genome sequence was downloaded from the European Nucleotide Archive (accession number ERP000042). S129/SvJae genome sequencing data was downloaded from the Sequence Read Archive (accession number SRX037820). Reads were aligned to the mm9 genome using Novoalign (www.novocraft.com) and using samtools (Li et al., Bioinformatics 25, 2078-2079 (2009)), and unmapped reads and PCR duplicates were filtered out. The final aligned datasets were processed using the Genome Analysis Toolkit (GATK) (McKenna et al., Genome Research 20, 1297-1303 (2010)). Specifically, Indel Realignment and Variant recalibration were performed. The GATK Unified Genotyper was used to make SNP and Indel calls. Inventors filtered out variants that did not meet the GATK quality filters or that were called as heterozygous variants, as the genome sequencing was performed in homozygous parental inbred mice. The genotype calls in the parents were used both to determine the extent of interactions in cis versus h-trans as well as in learning the phasing of hybrid CASTxJ129 cells a priori to haplotype reconstruction.

Hi-C Read Alignment

For Hi-C read alignment, Hi-C reads were aligned to the mm9 (mouse) or the hg18 (human) genome. In each case, any bases in the genome genotyped as SNPs in either Mus musculus castaneus or S129/SvJae (for mouse) or GM12878 (for humans) were masked. These bases were masked to "N"

in order to reduce reference bias mapping artifacts. Hi-C reads were aligned iteratively as single end reads using Novoalign. Specifically, for iterative alignment, first the entire sequencing read was aligned to either the mouse or human genome. Unmapped reads were then trimmed by 5 base pairs and realigned. This process was repeated until the read successfully aligns to the genome or until the trimmed read is less than 25 base pairs long. Iterative alignment is useful for Hi-C data because certain reads will span a proximity-ligation junction and fail to successfully align to the genome due to gaps and mismatches. Iteratively trimming unmapped reads allows these reads to align successfully to the genome when the trimming removes the part of the read that spans the ligation junction. After iterative alignment of reads as single ends is complete, the reads were manually paired using in-house scripts. Unmapped and PCR duplicate reads are removed. The aligned datasets were then finally subjected to GATK indel realignment and variant recalibration.

Analysis of Interaction Frequencies Between Homologous Chromosomes

When aligning the Hi-C data, a paired-end read could either have both ends mapped to the same chromosome (intra-chromosomal) or mapped to different chromosomes (inter-chromosomal). However, the initial mapping of the Hi-C data utilized a haploid reference genome and did not distinguish to which of the two homologous copies of a chromosome an individual sequencing read maps. As a result, read pairs that initially map as "intra-chromosomal" were broken down into reads that occur on the same homologous chromosome (which are truly in cis) and reads that map between the two homologous pairs (which was defined as "h-trans").

To determine the extent of reads that are in ci versus h-trans, it was first distinguished to which allele an individual read mapped. This was done by identifying reads that overlap with variant locations in the genome and then determining which allele the sequenced base at the variant location corresponds to. Once this information is obtained, the frequency with which regions interact in cis versus h-trans can be determined (see FIGS. 2c and 6).

Usable Coverage as Defined by Intra and Inter-Chromosomal Reads

For phasing using HapCUT, both intra-chromosomal and inter-chromosomal reads were utilized. For inter-chromosomal reads, one can consider each inter-chromosomal read pair as two single-end reads, as the paired information for such reads is not useful for phasing. In contrast, all intra-chromosomal reads are considered for phasing. The probability of a single read to harbor more than one variant is small, especially in humans where the variant density is relatively low. This, in combination with the fact that only the paired intra-chromosomal reads will have large insert sizes, means that the vast majority of reads that contribute to the success of haplotype phasing are the intra-chromosomal reads. Therefore, the "usable coverage" was defined as the genomic coverage derived from intra-chromosomal reads only.

The Hi-C experiment generated ~22% inter-chromosomal reads in CASTxJ129 while ~55% of the reads in GM12878 were inter-chromosomal. In other words, 620M paired-end reads out of 795M were useful in CASTxJ129, with a usable coverage of 30x. In humans, only 262M paired-end reads out of 577M were useful, resulting in a usable coverage of 17x. Thus, there was a lower usable coverage in humans despite a relatively similar total number of sequenced reads. In the inventors' experience, the fraction of all reads that are intra-chromosomal versus inter-chromosomal in a Hi-C experiment may vary between experiments and across cell types.

HaploSeq Using HapCUT

The HapCUT algorithm was used to perform the computational aspects of HaploSeq, the details of which are described previously in Bansal et al., Bioinformatics 24, i153-159 (2008). HapCUT was originally designed to work on conventional genome sequencing (WGS) or mate-pair data. HapCUT constructs a graph with the heterozygous variants as nodes and edges between nodes that are covered by the same fragment(s). Therefore, only fragments with at least two heterozygous variants are useful for haplotype phasing. HapCUT extracts such 'haplotype-informative' fragments from a coordinate sorted BAM file using a sorting method that stores each potential haplotype-informative read in a buffer until its mate is seen. The buffer size was customized to allow HapCUT handle large insert sized proximity-ligation reads.

HapCUT uses a greedy max-cut heuristic to identify the haplotype solution for each connected component in the graph with the lowest score under the MEC scoring function. In particular, the original HapCUT algorithm used O(n) iterations to find the best cut. Since Hi-C data resulted in chromosomal span haplotypes with a single large connected component, the default method took several days of computing time to phase the CASTxJ129 genome. To reduce the computation time, the impact of reducing the number of iterations on the accuracy of phasing was assessed. For CAST*129 system, it was observed that increasing the number of iterations beyond 1000 did not significantly improve the accuracy. For GM12878, up to 100,000 iterations were allowed. This solution was iterated multiple times and a maximum of 21 iterations in CASTxJ129 and 101 in GM12878 cells were used. The parameters in GM12878 cells allowed HapCUT to obtain higher accuracy given the lower variant density and reduced sequence coverage compared to the mouse data.

Maximum Insert Size Analysis

Figure 8A:
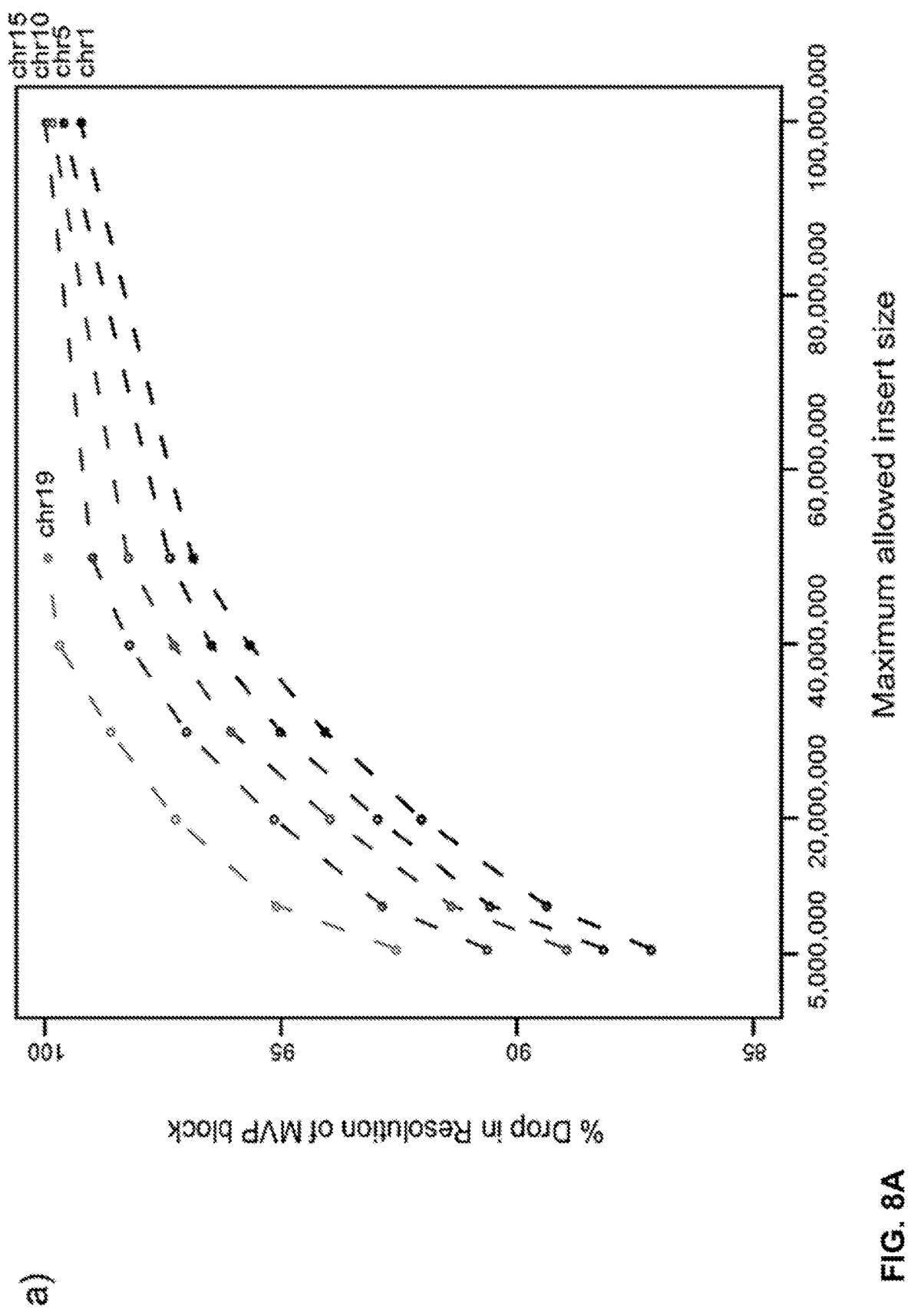
FIGS. 8a-b are a set of diagrams showing constrained HapCUT model allowing only fragments up to a certain maximum insert size (maxIS), where at higher maxIS, the resolution of MVP block (a) is high but contains higher accuracy (b).
Figure 8B:
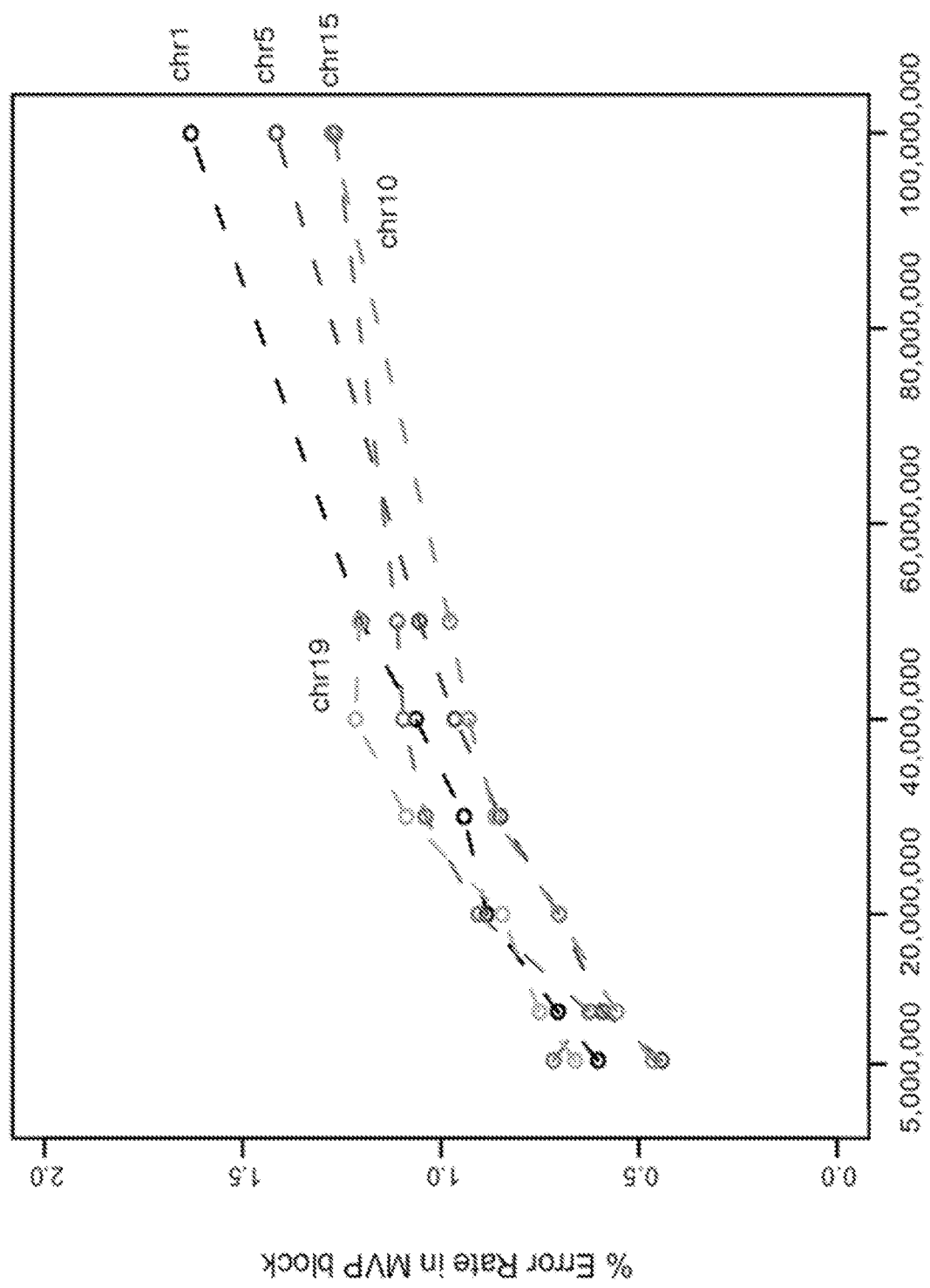

As previously mentioned the probability of a Hi-C read being in cis versus h-trans varies as a function of the distance between the two read pairs (FIG. 2c). At shorter genomic distances, the probability that an intra-chromosomal read is in h-trans is very low. At large distances (>30 Mbp), this probability rises substantially and is in theory more likely to introduce erroneous connections for HapCUT to phase. To account for this, the Hi-C data for chromosomes 1, 5, 10, 15 and 19 in the CASTxJ129 data were used and haplotype reconstruction repeated allowing variable maximum insert size values. Any reads where the insert size between reads was greater than the allowable maximum insert size were excluded. This analysis was performed using the low variant density case, for this analysis because lower density was most amenable for applications in humans (FIGS. 8a-b). This step resulted in an increase in accuracy of HaploSeq analysis with moderate reduction in resolution.

Insert Size Dependent Probability Correction

A useful feature of the HapCUT algorithm is that it accounts for the base quality score at a variant location in order to calculate the score of a potential haplotype. In other words, if in a sequencing read that links two variants and the base quality at one variant location is low, this read is given relatively lower weight by HapCUT in generating its final haplotype calls. Therefore, HapCUT can use this information to try to disregard potential sequencing errors from making erroneous haplotype connections. As previously mentioned, in Hi-C data errors may also arise due to h-trans interactions, which are much more frequent than sequencing errors and show a distance dependent behavior. Therefore, it was attempted to account for the likelihood of an interaction being in cis versus h-trans based on the distance between the two reads. The CASTx129 Hi-C data was used to identify reads that are in cis or h-trans. The insert-sizes was binned into 50 Kb bins and estimated the probability of a read being h-trans (#h-trans/(#cis+#h-trans). Local regression (LOWESS) was then used at 2% smoothing to predict h-trans probabilities at any given insert-size. For every intra-chromosomal read, the cis probabilities (1-h-lrans) were multiplied with the base qualities to account for the odds of this intra-chromosomal read being a homologous trans interaction. As a result, reads that are more likely to be h-trans are given lower weight by HapCUT in identifying the haplotype solution.

Adding h-trans interaction probabilities increases HaploSeq accuracy moderately, without having any effect on resolution. As a comparison, chromosome 19 maxIS of 30 Mb had an error rate of 1.1% (FIG. 8b). After adding h-trans probabilities, the error rate is 0.9% (FIG. 4b), where Error rate is defined as 1-Accuracy.

Local Conditional Phasing Simulation

In order to study the ability to perform local phasing at different percentages of resolution, a stepwise analysis was performed. First, seed haplotypes were generated at different resolutions. Then, Beagle (v4.0) (Browning et al., Genetics 194, 459-471 (2013)) was used to perform local phasing under the guidance of the seed haplotype. Finally, accuracy of local phasing was checked by comparing it to phasing information known a prioiri from 1000 genomes project.

To simulate seed haplotypes at different resolutions, seed genotypes were first simulated. Different combinations of read length and coverage were used to obtain seed genotypes of various resolutions. In particular, Hi-C intra-chromosomal read starting positions from H1 and H1-derived cells (unpublished data) were used to generate pairs of reads of a given read length and coverage. This allowed one to maintain the Hi-C data structure and the observed distribution of insert sizes in the simulated data. To generate the seed genotype, the inventors constructed a graph with nodes representing heterozygous variants in GM12878 (chromosome 1) and edges corresponding to reads that cover multiple variants. This graph is essentially a genotype graph because the phasing is not known yet. Hence, the whole point of this graph is to provide a subset of variants that are part of the seed genotype and that are not (gaps to be inferred by local phasing), based on the resolution and Hi-C data structure. Seed genotypes were generated at required parameters of read length and coverage to attain a specific resolution. These seed genotypes were used for both local phasing (FIG. 5a) and to study the minimal requirements for generating seed haplotypes of enough resolution (FIGS. 5c-d). These two analyses were performed independently and in both cases, generating seed genotypes and downstream analysis were repeated 10 times to note the average results.

To perform local conditional phasing, one needs an a priori haplotype system to check accuracy of the local conditional phasing. Because a priori haplotype information from the trio covers only ~65% of heterozygous variants, it was decided to perform local phasing simulation only on the trio subset. Specifically, it was conditioned that every variant that is part of either seed genotype or "gaps," should be part of 1000 genome phased trio. Seed genotypes were converted to seed haplotypes using the trio information while keeping "gap" variants as unphased. Local phasing conditioned on the seed haplotype was then used to infer phasing of the gap variants using Beagle. Homozygous variants were allowed to assist Beagle in making better predictions from the hidden Markov model.

To perform neighborhood correction for a seed haplotype unphased variant, the inventors collected 3 variants each upstream and downstream that are phased in seed haplotype. Then it was checked if there is 100% correlation between the phasing present in seed haplotype to what is predicted by Beagle. This gives a confidence of how well Beagle could have performed in this "local" region. If there is a 100% match, the variant was considered as conditionally phased. If there is not 100% match, the unphased variant was disregarded in the final haplotype. Other window sizes such as 5 and 10 were tried and no improvement in accuracy was found.

Local Conditional Phasing in Human GM12878 Cells

The inventors coupled HaploSeq analysis and local conditional phasing to increase resolution in GM12878 cells. Local conditional phasing was performed as described earlier on genotypes that are common between GM12878 (ref. 44) and population samples. In addition, as the seed haplotype is not 100% accurate, the inventors marked the seed haplotype phased variants that did not agree with local phasing. These marked variants were made "unphased" as these could be potential errors. Hence, apart from using neighborhood correction for deciding whether a gap variant needs to be locally phased (as in the simulation), the inventors also used this information to mark variants in the seed haplotype that could be potentially erroneous. This allowed a minor increase in accuracy after local phasing (see Table 1).

Overall HaploSeq accuracy is estimated as the fraction of heterozygous variants correctly phased in the MVP block after local phasing (FIG. 5b and Table 1. In particular, the inventors used only the variants phased in trio to estimate accuracy. For local phasing in chrX, the inventors made the male haploid genotypes as homozygous.

GM12878 cells have a lower variant density than CASTxJ129 and a lower coverage added more constraints on the prediction model resulting in relative higher HaploSeq error rate of 2%, when compared to 0.8% in low density CASTxJ129 case. A usable coverage of 25-30× (as shown in FIG. 5c-d) could help gain accuracy and potentially cover more rare variants in the seed haplotype. Currently, about 16% of the variants are not locally phased due to their absence in population. These could be phased either by additional Hi-C data or even conventional genome sequencing data, which can potentially link gap variants to variants in seed MVP block. An important aspect in HaploSeq analysis is the ability to form seed chromosome-span haplotype, which cannot be made from conventional genome sequencing or mate-pair or fosmids.

Fosmid Simulations

To simulate fosmid based sequencing (FIGS. 4b and c), the inventors emulated fosmid clones as paired end sequencing, with insert sizes close to 40 kb. The inventors reasoned that this approach is easier to simulate and yet maintains the data structure that fosmids add to haplotype reconstruction. As evidence, the simulation produces haplotype blocks of size up to 1 Mb in humans, as reported by other groups (Kitzman et al., Nature Biotechnology 29, 59-63 (2011); Suk et al., Genome Research 21, 1672-1685 (2011); and Duitama et al., Nucleic Acids Research 40, 2041-2053 (2012)).

To that end, simulated 100 bp paired-end reads were at various sequencing coverage for GM12878 chromosome 1. Reads were simulated with random starting positions with a mean insert size as mentioned and a standard deviation of 10% of the mean. Fosmid inserts represents simulations with "fosmid-size" insert to pinpoint the ability of these large fragments to generate longer haplotypes. 500 bp Skewed mix inserts contained 70% of 500 bp insert sizes, 20% mate-pair inserts and 10% 40000 bp inserts. 40000 bp skewes contained 70% 40000 bp inserts and 10% 500 bp inserts. The N50 defined span of 50% of haplotype blocks containing N50 span. Simulations were repeated for 10 times and noted average N50 in the Y axis. The results demonstrated that higher coverage alone cannot form longer haplotpes. Further, these data demonstrated longer the insert size fragments generate longer haplotypes.

Example 2 Experimental Strategies of HaploSeq

In HaploSeq, the inventors first performed proximity-ligation sequencing based on the previously established Hi-C protocol (Lieberman-Aiden et al., Science 326, 289-293 (2009)). Proximity-ligation was first performed in situ prior to the isolation of DNA from cells, as opposed to purified genomic DNA in other haplotyping approaches (FIG. 1a). Specifically, spatially proximal genomic regions were cross-linked in situ, digested with a restriction enzyme, re-ligated to form artificial fragments, which were subsequently isolated (FIG. 1a). The purified DNA fragments thus isolated may capture two distant genomic loci that looped together in 3D space in vivo (Dekker et al., Science 295, 1306-1311 (2002); Lieberman-Aiden et al., Science 326, 289-293 (2009); and Kalhor et al., Nature Biotechnology 30, 90-98 (2012)). Indeed, after shotgun DNA-sequencing of the resulting DNA library, paired-end sequencing reads have "insert sizes" that range from several hundred base pairs to tens of million base pairs, while other methods tend to generate "inserts" ranging from several hundreds to tens of kilobase pairs (FIG. 1a-b). Theoretically, the experimental approach in HaploSeq preserves haplotype information because it allows two regions of the same chromosome that are linearly far apart to be linked into a short and contiguous DNA fragment (FIG. 1a). While the short fragments generated in a Hi-C experiment can form small haplotype blocks, long fragments ultimately can link these small blocks together (FIG. 1c). With enough sequencing coverage, such an approach permits one to link variants in discontinuous blocks and assemble every such block to a single haplotype. Therefore, with proximity-ligation based methods to prepare DNA sequencing libraries one can reconstruct chromosome-span haplotype blocks.

One factor to be considered is that proximity-ligation can capture interactions both in cis within an individual allele and in trans between homologous and non-homologous chromosomes. While non-homologous trans interactions between different chromosomes do not affect phasing, interactions in trans between homologous chromosomes (referred to as h-trans hereafter) may complicate haplotype reconstruction if h-trans interactions were as frequent as cis interactions. Therefore, the inventors set out to determine the relative frequency of h-trans versus cis interactions in proximity-ligation sequencing data. To accomplish this, the inventors used hybrid mouse embryonic stem cell (ES) line derived from a cross between two inbred homozygous strains (Mus musculus castaneous (CAS) and 129S4/SvJae (J129)), for which the parental inbred whole genome sequences (WGS) were publicly available. As a result, the knowledge of the maternal and paternal haplotypes within this cells line are known a priori as a product of the breeding structure, and the frequency of interactions between alleles can then be explicitly tested. The inventors performed Hi-C experiment and generated over 620 million usable 75 base-pair paired-end reads from these hybrid ES cells, corresponding to 30× coverage of the genome.

Figure 6:
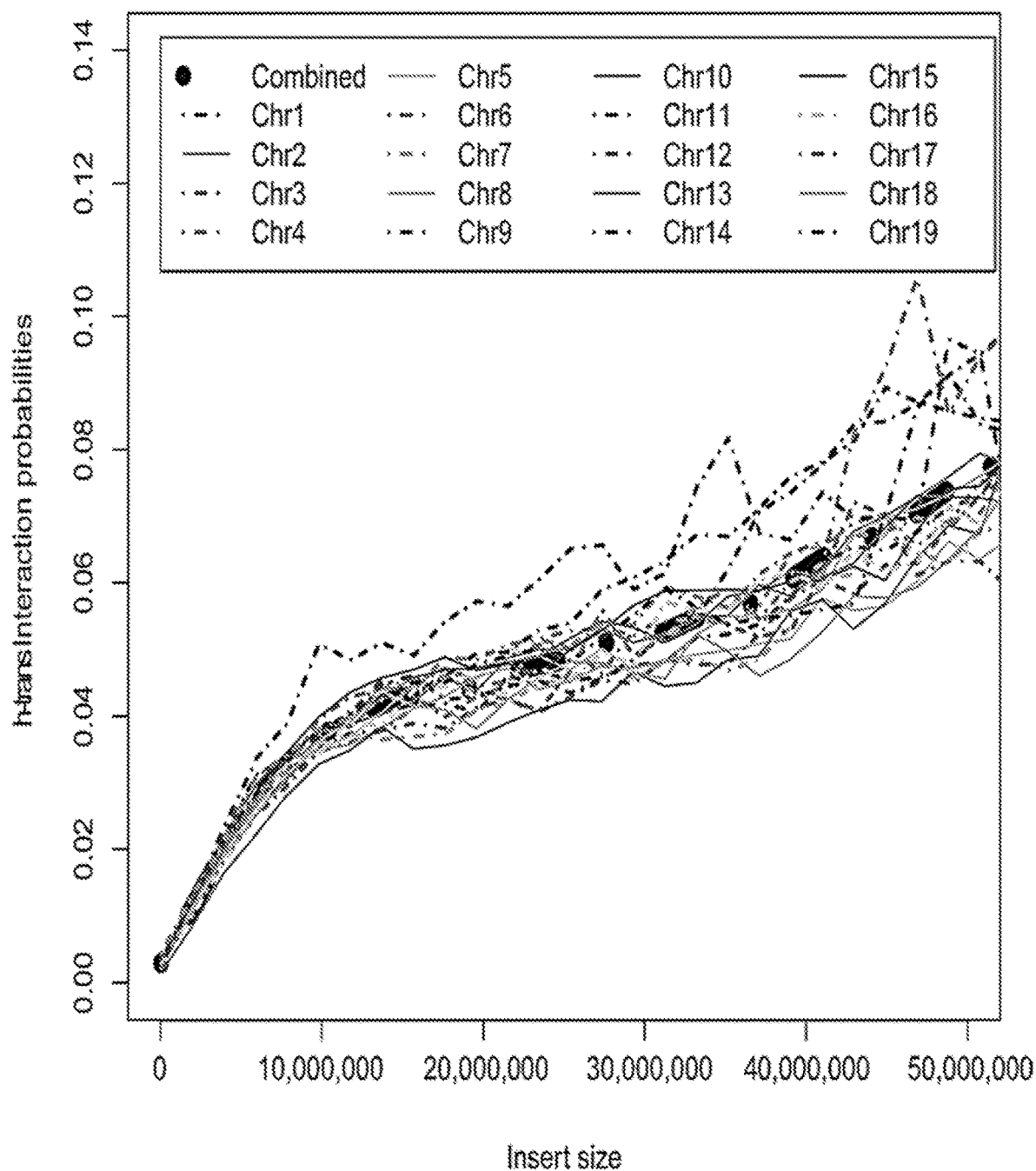
FIG. 6 is a diagram showing h-trans interaction probabilities of each CASTxJ129 chromosome plotted as a function of insert size.

To determine the extent of intra-haplotype (cis) versus inter-haplotype (h-trans) interactions, the inventors used the prior haplotype information to distinguish reads from CAST and J129 alleles. To examine the h-trans interaction patterns, the inventors at first visually checked the pattern of inter-actions between every allele (FIG. 2a). Previous Hi-C studies have confirmed the long established concept of chromosome territories, albeit without distinguishing between the two alleles for each chromosome (Lieberman-Aiden et al., Science 326, 289-293 (2009); and Kalhor et al., Nature Biotechnology 30, 90-98 (2012)). The inventors observed that the CAST and J129 alleles for each chromosome form individual chromosome territories (FIG. 2a). Further, the inventors observed <2% h-trans interactions when compared with cis interactions, indicating that the vast majority of Hi-C reads are truly in cis (FIG. 2b). In addition, the probability of a DNA read being in cis versus in h-trans appears to vary as a function of the insert size between the read pairs (FIG. 2c, and FIG. 6). As shown FIG. 6, each plot depicts lowess smoothened curve and the black plot results from combining all chromosomes. This shows that every chromosome follows a similar pattern of h-trans interaction probabilities. These observations indicate that the h-trans interactions are a rare phenomenon.

Example 3 Accurate Reconstruction of Chromosome-Span Haplotypes in the Hybrid Mouse ES Cells at High Resolution The existence of rare h-trans interacting reads and phenomena such as sequencing errors at the variant locations can cause erroneous connections between the homologous pairs and raise conflicts for haplotype reconstruction. To overcome these problems, the inventors incorporated HapCUT[5] software into HaploSeq analysis to probabilistically predict haplotypes. In particular, HapCUT constructs a graph with heterozygous variants as nodes and edges as explained by overlapping fragments. This graph might contain several spurious edges due to sequencing errors or h-trans interactions. HapCUT uses a max-cut algorithm to predict parsimonious solutions that are maximally consistent with the haplotype information provided by the set of input sequencing reads (FIG. 3a). Because proximity-ligation generates larger graphs than conventional genome sequencing or mate-pair, the inventors modified HapCUT to reduce its computing time, making it feasible for HaploSeq analysis. To test the ability of HapCUT to generate haplotype blocks from proximity-ligation and sequencing data, the inventors again utilized the CASTx129 mouse ES cell Hi-C data. In this instance, the inventors did not distinguish a priori to which allele a sequencing read belongs. Instead, the inventors allowed HapCUT to reconstruct de novo haplotype blocks of the heterozygous variants. The inventors then utilized the known haplotype information of the CAST and J129 alleles to assess the performance of the algorithm. The inventors used the metrics of completeness, resolution, and accuracy to assess the success of the HaploSeq analysis in haplotype reconstruction (FIG. 7).

Figures 7A, 7B, 7C, 7D:
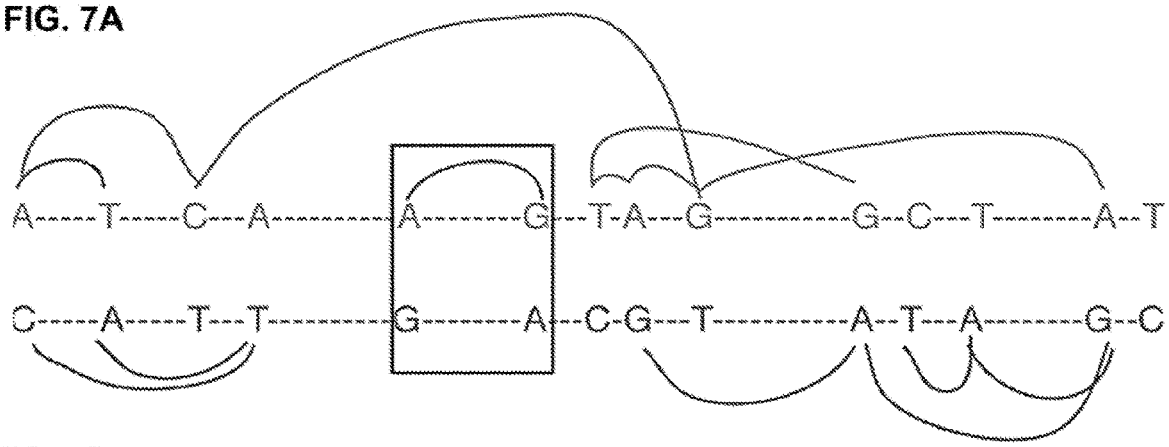
FIGS. 7a-d are a set of diagrams showing graphical explanation of completeness, accuracy, and resolution in haplotype phasing (a) nucleotide bases represent heterozygous SNPs while "-" represents no variability; (b) haplotype phasing of the MVP block demonstrating resolution; (c) true haplotypes known a priori and this knowledge helps to measure the accuracy of predicted de-novo haplotypes and inaccurate variant phasing is shown at the gray box location; (d) different metrics.

In FIG. 7a, heterozygous SNPs are considered as nodes, and edges are made between nodes that belong to same fragment. This graph system establishes two homologous chromosomes (or haplotypes) de-novo. Nevertheless, there can be multiple blocks formed and in this example, and the inventors had identified one large MVP component that spans 96.15% and one other small block that cannot be connected to MVP block (shown in the black edged box).

The completeness of haplotype phasing is measured by the size of the haplotype blocks generated in terms of the number of base-pairs spanned or by the total number of heterozygous variants spanned per block. In general, HapCUT will generate several haplotype blocks of various sizes for each chromosome depending on heterozygous variant connections. The haplotype block containing the most heterozygous variants phased (MVP) is generally the most interesting, as it is often the largest spanning block. In addition, a minority of heterozygous variants may be assigned to smaller blocks due to their inability to be connected with MVP block. The MVP block in this case spans greater than 99.9% of the phasable base-pairs for each chromosome (FIG. 3b), demonstrating that HaploSeq analysis using Hi-C data can generate complete chromosome-span haplotypes.

While completeness is defined as the base-pair span of MVP block, resolution is denoted as the fraction of phased heterozygous variants relative to the total variants spanned in the MVP block (FIG. 7). These MVP blocks generated for each chromosome are of high resolution, as the inventors could phase about 95% of the heterozygous variants on any given chromosome (FIG. 3b). The inability to link the remaining 5% of heterozygous variants is likely due to either the absence of sequencing fragments covering these variants or the inability to link these heterozygous variants to the MVP haplotype block. As a result, the MVP block, while spanning the majority of the chromosome, contains approximately 5% gaps in variants phased.

To assess the accuracy of the heterozygous variants within the MVP block, the inventors compared the predicted haplotypes generated de novo by HaploSeq analysis with the known haplotypes of the CAST and J129 alleles. The inventors define accuracy as the fraction of phased heterozygous variants that are correctly phased in the MVP block (FIG. 7). Of the variants that were assigned to MVP haplotype block, the inventors observed >99.5% accuracy in distinguishing between the two known haplotypes (FIG. 3b).

Lastly, as the inventors had previously demonstrated that the h-trans interaction probability increases with the genomic distance separating two sequencing reads (FIG. 2c), the inventors incorporated the h-trans interaction probabilities into the HapCUT algorithm and capped the maximum insert size for sequencing reads at 30 million base pairs. These conditions did not sacrifice the completeness of the haplotypes the inventors generated. Instead, the inventors observe a further improvement in the accuracy of the variants in the MVP block with a modest reduction of the resolution of the variants phased (FIGS. 8a and b).

As shown in these figures, constrained HapCUT model allowed only fragments up to a certain maximum insert size (maxIS). The lowest maxIS was 5 megabases, below which the ability to form chromosome-span haplotypes in MVP block is lost. At higher maxIS, the resolution of MVP block (a) is high but contains higher accuracy (b). Hence, 30 megabases was chosen as the maxIS as to allow acceptable levels of resolution and accuracy. This simulation was performed in different chromosomes in CASTxJ129 system in the low variant density scenario, as this was more close to human applications. This analysis did not incorporate the h-trans probabilities, so that the effect of maxIS alone is realized.

In summary, these results demonstrate that HaploSeq analysis yields complete, high resolution and accurate haplotypes for all autosomal chromosomes.

Example 4 Comparisons of HaploSeq with Other Haplotype Phasing Methods

To compare the method disclosed here with previous established haplotyping methods, the inventors simulated 20×coverage DNA sequencing data for conventional paired-end shotgun DNA sequencing (WGS), mate-pair sequencing, fosmids and proximity-ligation to assess each method's ability to reconstruct haplotypes. The inventors observed that only HaploSeq analysis using proximity-ligation could generate a chromosome-span MVP block, while other methods generated significantly smaller MVP blocks and thus have a fragmented haplotype structure (FIG. 3c). In particular, mate-pair and fosmids based sequencing approaches generated blocks of few hundred kilobases and about a megabase in size, respectively. The inventors combined WGS data with mate pair, fosmids and proximity-ligation to increase coverage and add variability in data structure, and yet the ability to generate longer haplotypes did not change significantly (FIG. 3c). To compare the resolution of the methods, the inventors examined the cumulative adjusted span of the top 100 variant-phased haplotype blocks (FIG. 3d), where adjusted span is denoted as the product of completeness and resolution. The MVP block alone obtained in HaploSeq was complete and had ~90% resolution. In contrast, conventional shotgun sequencing, mate pairs and fosmids can only cover 5%, 65%, and 90% of the chromosome when all blocks are considered cumulatively. Cumulative completeness is of less potential usage than the size of the MVP block since variants in different blocks remain unphased with each other. Higher coverage (dashed lines, FIG. 3d) did not significantly change the cumulative span pattern. This shows that total sequencing coverage appears to be less important than the method used for phasing in order to generate chromosome-span haplotype blocks.

Example 5 HaploSeq Performance Depends on Variant Density

A distinct feature of the CASTxJ129 ES cell line is the high density of heterozygous variants throughout the genome. On average, there is a heterozygous variant every 150 bases, which is 7-10 times more frequent than in humans (Wheeler et al., Nature 452, 872-876 (2008) and Pushkarev et al., Nature Biotechnology 27, 847-850 (2009)) (FIG. 4a). To initially test the feasibility of HaploSeq to generate haplotypes in human cells, the inventors sub-sampled heterozygous variants in CASTxJ129 system so that the variant density mimics that in human populations. The inventors then tested how lower variant density affects the ability of HaploSeq to reconstruct haplotypes. While a reduced variant density rapidly decreases the ability of fragments to harbor heterozygous variants, the ability to obtain accurate and complete haplotype blocks by HaploSeq did not change (FIG. 4b). The inventors still observed complete haplotypes over each chromosome, and the average accuracy decreased only marginally, from ~99.6% to ~99.2% in low variant density case (FIG. 4b). However, a lower variant density did result in less usable reads, which in turn provides lesser opportunities for the prediction model to resolve haplotypes. As a result, the MVP block generated using "human" variant density has lower resolution with fewer variants phased compared to high-density condition.

Approximately 32% of heterozygous variants are now phased in the MVP block (FIG. 4b), instead of 95% in the high-density case (FIG. 3b). In summary, low variant density does not affect completeness or accuracy, but does affect the resolution of chromosome-span haplotypes by HaploSeq analysis.

Example 6 HaploSeq Analysis of a Human Individual

To realistically assess the ability of the method here to phase haplotypes in humans, the inventors performed HaploSeq in the GM12878 lymphoblastoid cell line. The complete haplotype of this cell line has been determined by the 1000 genomes project from family trio WGS[15]. The inventors generated over 262 million usable 100 base pair paired-end reads corresponding to ~17×coverage. HaploSeq successfully generated chromosome-span haplotypes in all acrocentric chromosomes and in 17 out of 18 metacentric chromosomes in the GM12878 cells (FIGS. 4c-d). Of note, previous methods attempting haplotype reconstruction in humans are unable to reconstruct haplotypes spanning across the highly repetitive centromeric regions of metacentric chromosomes (Levy et al., PLoS Biology 5, e254 (2007); Kitzman et al., Nature Biotechnology 29, 59-63 (2011); Suk et al., Genome Research 21, 1672-1685 (2011); Duitama et al., Nucleic Acids Research 40, 2041-2053 (2012); and Kaper et al., Proc Natl Acad Sci USA 110, 5552-5557 (2013)). Using HaploSeq, the inventors generated haplotypes that spanned the centromere in all metacentric chromosomes with the exception of chromosome 9, where an erroneous linkage causes switching of haplotype calls at the centromere. In addition to having a large 15 Mbp poorly mapped centromere region, chromosome 9 has relatively lower usable coverage (13.7×). The inventors hypothesized that additional coverage might offer a better chance in spanning the centromere. Therefore, the inventors combined the Hi-C data with previously generated Hi-C and TCC data in chromosome 9, which increased its coverage to ~15×. Tethered chromatin capture (TCC) is similar to Hi-C where the cross-linked DNA fragments are tethered and ligated together on a solid surface. TCC generates similar data as a Hi-C experiment with slightly better ability to capture true long-range chromatin interactions (Kalhor et al., Nature Biotechnology 30, 90-98 (2012)). Using this combined dataset, the inventors were able to accurately phase the entire chromosome 9. In summary, the inventors generated complete chromosome-span haplotypes, for all human chromosomes including chromosome X, albeit at reduced resolution of ~22% (FIG. 4c), from just 17×genome coverage of HaploSeq analysis.

Example 7 Complete and High Resolution Haplotype Phasing by Combining HaploSeq and Local Conditional Phasing While HaploSeq generated complete chromosome span haplotypes, it was unable to achieve a high resolution of variants phased due to the low variant density in a human population. This resulted in "gaps" where heterozygous variants remained unphased relative to the MVP haplotype block. The inventors reasoned that these gap variants could be probabilistically linked to the MVP block using linkage disequilibrium patterns derived from population scale sequencing data. For this purpose, the inventors used the Beagle (v4.0) (Browning et al., Genetics 194, 459-471 (2013)) software and sequencing data from the 1000 genomes project (Genomes Project, C. et al., Nature 491, 56-65 (2012)). The inventors used the HaploSeq generated chromosome-span haplotype as a "seed haplotype" to guide the local phasing. As a result, the inventors could generate local phasing predictions from linkage disequilibrium (LD) measures for the remaining unphased "gapped" variants relative to the MVP block.

To initially investigate the effectiveness of this approach, the inventors simulated chromosome-span seed haplotypes in the GM12878 genome with different percentages of resolution in terms of the number of variants phased in the MVP block. The simulation results indicate that the inventors can accurately infer local phasing even at low-resolution seed haplotype inputs (3% error at 10% seed haplotype resolution, upper curve in FIG. 5a). Due to complex population structures, occasional mismatch occurs between phase predictions from local haplotypes predicted by Beagle and the HaploSeq seed haplotype. To correct this phenomenon, the inventors checked a neighborhood window region surrounding every heterozygous variant to be inferred and analyzed the agreement in phasing between seed haplotype and local phasing. By only accepting variants as being phased relative to the seed haplotype if they have a 100% agreement, the inventors could reduce the error rate to ~0.7% regardless of seed haplotype resolution (lower curve, FIG. 5a). Because of this, the fraction of heterozygous variants for which the inventors can infer local phasing increases with greater seed haplotype resolution (bottom panel, FIG. 5a). The inventors used a neighborhood window size of 3 phased seed haplotype variants, and an increase in window size did not increase accuracy significantly.

Based by these results, the inventors used the MVP chromosome-span haplotypes generated from HaploSeq analysis as seed haplotypes and performed local conditional phasing. Overall, the inventors generated chromosome-span haplotypes with ~81% resolution at an accuracy of ~98%, on average (FIG. 5b). Notably, among the 19% heterozygous variants that cannot be locally phased, ~16% were due to their absence in population samples and ~3% because of neighborhood correction, which only marginally affects resolution (FIG. 5b). Therefore, by coupling HaploSeq analysis and local conditional phasing, the inventors were able to achieve high resolution and accurate chromosome-span haplotypes in humans.

Example 8 Requirements to Obtain Accurate and High-Resolution Chromosome-Span Haplotypes by HaploSeq From the local conditional phasing analysis, the inventors deduced that a seed haplotype with ~20-30% resolution is sufficient to obtain accurate and high-resolution chromosome-span haplotypes. A subsequent question therefore is what are the minimal experimental requirements to achieve chromosome-span seed haplotypes with ~20-30% resolution. To investigate this, the inventors generated simulated proximity-ligation sequencing data with varying read length and sequencing coverage. Based on the simulations, to first achieve chromosome-span haplotypes depends on obtaining a usable sequencing coverage of ~15×, irrespective of the read length (FIG. 5c). After obtaining chromosome span-haplotypes, achieving the desired fraction of ~20-30% resolution would require approximately 25-30× usable coverage with 100 base-pair paired-end reads (FIG. 5d). The simulation also emphasizes the need for longer read lengths, as longer read lengths increase seed haplotype resolution significantly. In addition, this simulation did not take accuracy into account and yet from the analysis of GM12878 cells, the inventors could deduce that the ability to reconstruct accurate haplotypes depends on usable coverage. For instance, low coverage chromosomes such as 17 and 19, have a relatively lower accuracy. In particular, lower coverage might cause many variants to be linked with fewer edges, which in turn can propagate high error structures to the entirety of chromosome-span haplotypes. See Table 1 below.

Table 1 shows the relationship between coverage and accuracy of MVP blocks. Low coverage affects the ability of proximity-ligation to achieve accurate haplotypes as seen in chromosomes 17, 19 and 20. After local conditional phasing (LCP), resolution was increased from 22% to 81% (FIG. 5b) without reducing accuracy further. In fact, a minor increase was seen in accuracy based on neighborhood correction. The last column reflects overall accuracy, as also shown in FIG. 5b.

Furthermore, while the inventors did not reach ~25× usable coverage for any of the chromosomes, the inventors could still achieve about ~98% accuracy on average. Additional coverage can increase accuracy even further, as observed in low-density CASTxJ129 system. Therefore, 25-30× usable coverage with 100 base pair paired-end reads is sufficient to achieve chromosome-span haplotypes with ~20-30% resolution and allow accurate local conditional phasing using HaploSeq analysis.

TABLE 1

| Chr | Usable Coverage | Percentage MVP Block Accuracy Before LCP | Overall accuracy of MVP block after LCP (as in FIG. 5b) |
| --- | --- | --- | --- |
| chr1 | 17.708 | 97.520 | 98.164 |
| chr2 | 20.683 | 97.514 | 98.214 |
| chr3 | 20.563 | 98.067 | 98.616 |
| chr4 | 20.163 | 97.963 | 98.459 |
| chr5 | 19.813 | 97.979 | 98.516 |
| chr6 | 20.419 | 97.249 | 98.132 |
| chr7 | 17.958 | 97.944 | 98.445 |
| chr8 | 18.777 | 98.543 | 98.766 |
| chr9 | 14.749 | 97.855 | 98.099 |
| chr10 | 17.537 | 98.480 | 98.743 |
| chr11 | 17.776 | 98.184 | 98.474 |
| chr12 | 18.649 | 98.043 | 98.602 |
| chr13 | 18.462 | 97.993 | 98.429 |
| chr14 | 17.507 | 98.170 | 98.714 |
| chr15 | 16.332 | 97.319 | 98.052 |
| chr16 | 12.390 | 97.455 | 97.945 |
| chr17 | 14.659 | 94.622 | 95.368 |
| chr18 | 17.900 | 96.256 | 98.548 |
| chr19 | 9.717 | 95.695 | 95.985 |
| chr20 | 14.386 | 97.484 | 96.901 |
| chr21 | 14.639 | 98.346 | 98.345 |
| chr22 | 11.107 | 97.181 | 97.843 |
| chrX | 16.760 | 95.660 | 96.489 |

Example 9 HaploSeq Analysis of Human Individuals

In this example, HaploSeq analysis was carried out using samples from four human individuals. To that end, human tissue samples were flash frozen and pulverized prior to formaldehyde cross-linking. Hi-C was then conducted on the samples as described in Lieberman-Aiden et al., Science 326, 289-293 (2009). Haplotyping was performed using the previously described HaploSeq method (Selvaraj et al., Nat Biotechnol. 2013 December; 31(12):1111-8). Briefly, Hi-C reads from each donor were used as input sequencing into the HapCUT software (Bansal et al., Bioinformatics. 2008 Aug. 15; 24(16):i153-9) in order to generate haplotype predictions. For final haplotype calls, Hi-C data was combined with WGS mate-pair data for the donor genomes. Because Hi-C data can phase only some of the SNPs, the local conditional phasing procedure was performed by utilizing population sequencing data from the 1000 genomes project. HaploSeq generates two haplotypes for each chromosome, one for the maternal allele and one for the paternal allele. One allele is named as P1 (parent1) and another allele is named as P2 (parent2) since information regarding the parent of origin in each donor genome was not available.

For four different tissue donors, the inventors were able to generate haplotypes spanning entire chromosomes with 99.5% completeness (the coverage of haplotype resolved genomic regions) on average and with an average resolution (the coverage of phased heterozygous SNPs) ranging from 78% to 89% in each tissue donor. The accuracy of haplotype predictions was validated by comparing the concordance of predicted haplotypes with the SNPs residing in the same paired-end sequencing reads. The concordance rates were 99.7% for H3K27ac ChIP-seq reads and 98.4% for mRNA-seq reads indicating a high degree of accuracy.

Example 10 Targeted Haplotyping Using Capture-HiC and Sequencing

In this example, Capture-HiC with oligonucleotide probes was used to capture chromatin interactions for targeted haplotyping of the entire human HLA locus.

To generate Hi-C libraries, GM12878 (CORIELL) cells were cultured in suspension in 85% RPMI media supplemented with 15% FBS and 1× penicillin/streptomycin. GM12878 cells were harvested, formaldehyde fixed, and subject to the Hi-C protocol as described in Lieberman-Aiden et al. Science 326, 289-293, (2009), with some modifications prior to capture sequencing. After Illumina adapters were ligated onto Hi-C fragments, libraries were subjected to 14 cycles of PCR amplification prior to capture hybridization using a high-fidelity (Fusion) polymerase. The number of pre-capture PCR cycles can be tailored depending on how much DNA is required for downstream capture hybridization reactions. In this case, several parallel PCR reactions were performed using small amounts of bead-bound Hi-C library input at 14 cycles to maximize PCR yield and to obtain sufficient material for reproducible Capture-HiC experiments. NGS was performed on the pre-capture (14 cycle) libraries in order to examine library quality and to provide an internal depth-matched control for Capture-HiC libraries.

Using the protocols described above, a conventional Hi-C library was first generated with enough material to enable oligonucleotide probe based capturing of the entire HLA region (FIG. 9 and FIG. 10a).

To obtain targeted haplotyping of the human HLA locus, oligonucleotide probe sequences were computationally generated and targeted the non-repetitive +/−400 bp regions adjacent to HindIII cut sites over the HLA locus (FIG. 10). For that, a haplotyping performance simulation was carried out. Briefly, HaploSeq performance was simulated in terms of haplotyping resolution (Y-axis) as a function of sequencing coverage (x-axis). This study was performed to more generally ask how well HaploSeq would perform if only Hi-C fragments containing HindIII cut site-adjacent sequences were present in the library. In theory, a Capture-HiC library would only contain Hi-C fragments in which at least one read-end originated from a HindIII cute site-adjacent sequence. Therefore, using an in-house conventional Hi-C dataset, HaploSeq analysis was performed using all mapped Hi-C reads without restricting any of the reads (Resolution_Nores). The usable reads were also restricted to only those containing at least 1 read end within 500 bp of a HindIII cut site (Resolution_pm500) or 250 bp of a cut site (Resolution_pm250). Results from this simulation indicated that although there was a ~20% decrease in haplotyping resolution, the resolution would still be sufficient for haplotyping purposes. The results also indicated that there was minimal difference in resolution whether the reads were restricted to 250 bp or 500 bp adjacent to HindIII cut sites. Accordingly, 400 bp was chosen for the targeted approach.

Using SureDesign parameters, probes were designed at 4×tiling density at the target regions to optimize capture efficiency and consequently maximizing haplotyping resolution and accuracy. More specifically, to generate RNA baits, probes were designed using the SureDesign software suite (AGILENT TECHNOLOGIES). The custom design targeted the upstream and downstream 400 bp adjacent to HindIII cut sites spanning the MHC locus using the hg19 genome build (chr6:29689001-33098938). SureDesign parameters were set to 4×tiling density, maximum probe boosting, and maximum repetitive sequence masking. Despite not being adjacent to HindIII cut sites, the inventors also targeted HLA gene exons at 2×tiling density, balanced boosting, and maximum repetitive element masking. In sum, 12,298 probes were computationally generated by SureDesign using design parameters described herein.

Next, single-stranded DNA (ssDNA) oligos were synthesized by CustomArray Inc. ssDNA oligos contained universal forward and reverse priming sequences. Forward priming sequences comprised of a truncated SP6 RNA polymerase recognition sequence. The reverse universal priming sequence contained a BsrDI recognition sequence for 3' cleavage prior to in vitro transcription. To convert oligos into biotinylated RNA baits, oligos were diluted and then PCR-amplified using high-fidelity DNA polymerase (KAPA) and then column-purified (PROMEGA). The PCR reaction also served to fill in the remainder of the SP6 recognition sequence. Next, reverse priming sequences were removed by digesting the dsDNA with BsrDI (New England Biosciences) and purified again to remove the digested fragment. Lastly, in vitro transcription (IVT) was performed according to manufacturer's protocol (AMBION) in the presence of biotinylated UTP (EPICENTRE). RNA was then column-purified (QIAGEN), diluted to working concentration (500 ng/µl) and stored at −80° C. until use.

To enrich the Hi-C libraries for Hi-C fragments mapping to the HLA locus, capture hybridization was performed followed by PCR amplification primarily according to a CustomArray protocol with some modifications. Briefly, 500 ng of Hi-C library was incubated overnight at 65° C. with 500 ng of biotinylated RNA probe. Because the targeted sequence (~320 kb) is only ~0.01% of the genome, the inventors carried out 16 parallel hybridization reactions per experiment and pooled the final hybridization products prior to sequencing. Then, RNA:DNA hybrids were pulled down using streptavidin coated beads (INVITROGEN), non-bound DNA fragments were washed away, and captured products were eluted. After captured products were eluted, they were desalted on QIAGEN MinElute columns, and PCR amplified (FUSION) using 11 cycles. In this procedure, all steps were carried out independently for each hybridization reaction. In other words, several parallel post-capture PCR reactions were performed on the desalted captured fragments, and each post-capture PCR product was purified independently using AMPure XP beads (Beckman Coulter). PCR products were then pooled and then concentrated using a speed-vac. The resulting Capture-HiC libraries were then subject to next-generation sequences on Illumina HiSeq2500.

More specifically, after preparing the Capture Hi-C library, the resulting library was sequenced at ~1× sequencing depth, using paired-end 100 bp read lengths. In theory, this sequencing depth would be enough to cover each base in the genome once. The coverage over the entire HLA locus (including all non-targeted sequences across the locus) was then computed and determined to be ~32.1×. To compute the HLA locus enrichment, the HLA coverage was divided by the genomic coverage. All monoclonal mapped reads from the Capture-HiC sequencing data were binned into 100 kb bins genome wide. Here, the total number of reads falling into each bin at the HLA locus and the adjacent off-target region on chromosome 6 was plotted. It was found that the targeted HLA locus was approximately from 29 M to 33.4 M, which displays significant enrichment relative to non-targeted adjacent regions on chromosome 6.

In sum, by performing the above-described capture sequencing on the Hi-C library, a Capture-HiC library of the GM12878 human lymphoblastoid cell line (LCL) was generated at ~1.1×sequencing depth with ~30-fold enrichment over the HLA locus.

As haplotyping efficacy depends on the fidelity of 3D chromosomal contacts, it was investigated whether Capture-HiC datasets preserved the relative contact frequencies compared to a conventional Hi-C library at the same locus. To that end, chromatin interactions from Capture Hi-C were compared with previously published Hi-C data at the HLA locus from GM12878 cells. Briefly, contact matrices were generated over the HLA locus in 20 kb bins using Capture-HiC data from GM12878 (top), and published data from GM12878 (Selvaraj et al., Nat Biotechnol. 2013 December; 31(12):1111). Prior to generating contact matrices, each dataset was normalized by read depth, which simply divides each matrix value (I,j) by the total number of reads mapping to the locus. It was found that there was a highly significant concordance between these datasets ($p<0.01$).

In addition to examining whether the relative 3D contact frequencies were preserved in Capture-HiC data, assays were also performed to examine the Hi-C fragment characteristics more closely. First, using all Capture-HiC data (including off-target sequences captured by the experiment), the inventors compared the proportion of intrachromosomal (cis) and interchromosomal (trans) reads in the Capture and Conventional Hi-C libraries and found the cis:trans ratios to be consistent with each other. Second, if each dataset was restricted to only reads mapping to the HLA locus, it was again found that each dataset contained roughly the same cis:trans ratio. Third, as HaploSeq is critically dependent on a high frequency of ciscontacts occurring within the same homologous chromosome (h-cis) (~99%), the h-cis rate in the Capture-HiC data was explored. It was found that Capture-HiC data also contained an overwhelming majority (about 98%) of h-cis Hi-C fragments, thus enabling effective HaploSeq analysis. This analysis revealed that conventional Hi-C and Capture-HiC libraries generally have comparable cis:trans read ratios and that Capture-HiC has similar homologous-trans interactions, thus preserving the intra-haplotype contact frequencies, which is critical to maintain high haplotyping accuracy using HaploSeq.

In addition, analysis of Capture-HiC RNA probe sensitivity was carried out. As metrics to evaluate the performance of the Capture-HiC probes, the inventors analyzed the read density over each probe sequence as well as the total fraction of probes with at least 1 captured Hi-C fragment. To that end, the read density (Y-axis) was plotted for each unique RNA probe sequences (X-axis) to generate a histogram. Each vertical line in this histogram represents a single unique probe. It was found that of all 7,885 total unique probes, 7,650 (~97%) had a least one read mapping to the sequence targeted by the probe. This provides some sense of the overall sensitivity of the capture sequencing approach.

Taken together, the above results shown that the Capture-HiC protocol data was of high quality data and therefore enables accurate analyses of haplotype patterns.

Next, haplotype reconstruction from Capture-HiC data was performed using HaploSeq (Selvaraj et al., Nat Biotechnol. 2013 December; 31(12):1111-8) and LCP protocols. First, phasing information for GM12878 was obtained from previously published data (Genomes Project, C. et al. *Nature* 467, 1061-1073, (2010)). Then, the HaploSeq and the local conditional phasing (LCP) protocols were utilized to generate a single haplotype structure over the HLA locus and phased ~95% of alleles in GM12878. The haplotyping results from HaploSeq analysis are summarized in the table below. The predicted haplotype structure was then compared with previously reported haplotype structures and estimated the accuracy of Capture-HiC to be ~97.7% (see Table 2 below).

TABLE 2

| Haplotyping Results | |
|---|---|
| Completeness | 100% |
| Resolution | 4210/9112 (46.2%) |
| Accuracy | 4043/4210 (96.0%) |
| Haplotyping Results after LCP | |
| Completeness | 100% |
| Resolution | 8636/9112 (94.8%) |
| Accuracy | 8439/8636 (97.7%) |
| HAPCUT Accuracy | 4039/4206 (96.0%) |
| IMPUTATION Accuracy | 4400/4430 (99.3%) |

As shown in the table, after HapCUT, the inventors generated a complete haplotype structure of the HLA locus and phase ~46% of all heterozygous SNPs at ~96% accuracy. After LCP, ~95% of all heterozygous SNPs were phased at ~98% accuracy. Of the final haplotypes structure, the accuracies of the SNPs phased by HapCUT and LCP were found to be ~96% and 99%, respectively.

Notably, the method disclosed herein is the first to demonstrate high-quality haplotyping across the entire HLA locus, phasing not only the highly diverse major and minor HLA allele loci, but also other important immunological genes and non-HLA genes across the locus together in a single haplotype structure. More broadly, this methodology is among the first to achieve complete haplotype structure of a user-defined targeted loci (Kaper et al. *Proc Natl Acad Sci USA* 110, 5552-57 (2013)). By achieving accurate haplotypes (~98%) for 95% alleles, this approach can be used in personalized genomics and population genetics.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method for haplotyping one or more chromosomes of a eukaryotic organism, the method comprising:
   providing a cell of the organism that contains a set of chromosomes having genomic DNA;
   incubating the cell or the nuclei thereof with a fixation agent for a period of time to allow crosslinking of the genomic DNA in situ and thereby to form crosslinked genomic DNA;
   fragmenting the crosslinked genomic DNA;
   ligating the proximally located crosslinked and fragmented genomic DNA to form a proximally ligated complex having a first genomic DNA fragment and a second genomic DNA fragment,
      wherein the first genomic DNA fragment and the second genomic DNA fragment are on the same chromosome, and
      wherein the first genomic DNA fragment and the second genomic DNA fragment are apart in situ by at least 100 bp;
   shearing the proximally ligated complex to form proximally-ligated DNA fragments;
   obtaining a plurality of the proximally-ligated DNA fragments to form a library;
   sequencing the plurality of the proximally-ligated DNA fragments to obtain a plurality of sequence reads and
   assembling the plurality of sequence reads to construct a haplotype for one or more of the chromosomes.

2. The method of claim 1, further comprising isolating the cell nuclei from the cell before the incubating step.

3. The method of claim 1, further comprising purifying ligated genomic DNA before the fragmenting step.

4. The method of claim 1, further comprising after the fragmenting step
   labeling the first genomic DNA fragment or the second genomic DNA fragment with a marker;
   joining the first genomic DNA fragment and the second genomic DNA fragment so that the maker is there between to form a labeled chimeric DNA molecule; and
   shearing the labeled chimeric DNA molecule to form labeled, proximally-ligated DNA fragments.

5. The method of claim 1, wherein the fragmenting step is carried out by digesting the ligated genomic DNA with a restriction enzyme to form digested genomic DNA fragments.

6. The method of claim 1, wherein the fixation agent comprises formaldehyde, glutaraldehyde, or formalin.

7. The method of claim 4, wherein the labeling step is carried out by filling the ends of said first or second genomic DNA fragment with a nucleotide that is labeled with the marker.

8. The method of claim 7, wherein the marker comprises a specific moiety having a unique affinity for a ligand.

9. The method of claim 4, wherein the joining step is carried out by ligating the first genomic DNA fragment and the second genomic DNA fragment using a ligase.

10. The method of claim 9, wherein the ligating is performed in solution or on a solid substrate.

11. The method of claim 1, wherein the sequencing is carried out using pair-end sequencing of pair end sequencing fragments.

12. The method of claim 11, wherein each pair-end sequencing read fragment is at least 20 bp in length.

13. The method of claim 1, wherein, for each chromosome, the library contains at least 15×sequence coverage.

14. The method of claim 1, wherein the organism is a fungus, a plant, an animal, a mammal, or a mammalian embryo.

15. The method of claim 14, wherein the organism is a human or a human embryo.

16. The method of claim 1, wherein the cell is a diploid cell, an aneuploid cell, or cancerous cell.

17. A method for targeted haplotyping an eukaryotic organism, the method comprising:

providing a cell of the organism that contains a set of chromosomes having genomic DNA;

incubating the cell or the nuclei thereof with a fixation agent for a period of time to allow crosslinking of the genomic DNA in situ and thereby to form crosslinked genomic DNA;

fragmenting the crosslinked genomic DNA;

ligating the proximally located crosslinked and fragmented DNA to form a proximally ligated complex having a first genomic DNA fragment and a second genomic DNA fragment, wherein the first genomic DNA fragment and the second genomic DNA fragment are on the same chromosome, and wherein the first genomic DNA fragment and the second genomic DNA fragment are apart in situ by at least 100 bp;

shearing the proximally ligated complex to form proximally-ligated DNA fragments;

contacting the proximally-ligated DNA fragments with one or more oligonucleotides that hybridize to preselected regions of a subset of the proximally-ligated fragments to provide a subset of proximally-ligated fragments hybridized to the oligonucleotides, separating the subset of proximally-ligated fragments from the oligonucleotides;

sequencing the subset of proximally-ligated DNA fragments to obtain a plurality of sequence reads and assembling the plurality of sequence reads to construct a targeted haplotype.

18. The method of claim 17, wherein the oligonucleotides are immobilized on a solid substrate.

* * * * *